United States Patent
Woodward

(10) Patent No.: US 9,707,047 B2
(45) Date of Patent: Jul. 18, 2017

(54) CHEMICAL GEL TO DISSOLVE METAL AND HAZARDOUS MEDICAL SHARPS

(71) Applicant: (Mac) Malcolm Philemon Woodward, Charlottesville, VA (US)

(72) Inventor: (Mac) Malcolm Philemon Woodward, Charlottesville, VA (US)

(73) Assignee: COMMONWEALTH INVESTMENT GROUP, Charlottesville, VA (US)

( * ) Notice: Subject to any disclaimer, the term of this patent is extended or adjusted under 35 U.S.C. 154(b) by 0 days.

(21) Appl. No.: 14/970,245

(22) Filed: Dec. 15, 2015

(65) Prior Publication Data

US 2017/0165024 A1    Jun. 15, 2017

(51) Int. Cl.
| | |
|---|---|
| *A61L 2/18* | (2006.01) |
| *A61B 50/36* | (2016.01) |
| *A61L 2/16* | (2006.01) |
| *A61B 50/00* | (2016.01) |

(52) U.S. Cl.
CPC ............ *A61B 50/362* (2016.02); *A61L 2/16* (2013.01); *A61B 2050/005* (2016.02); *A61B 2050/364* (2016.02)

(58) Field of Classification Search
CPC ....................................................... B65D 83/05
USPC ................... 588/313; 516/98; 206/210, 454; 604/199
See application file for complete search history.

(56) References Cited

U.S. PATENT DOCUMENTS

| | | | | |
|---|---|---|---|---|
| 3,937,667 | A * | 2/1976 | Scott | C22B 3/0097 252/635 |
| 5,145,063 | A * | 9/1992 | Lee | A61B 50/362 206/364 |
| 5,758,775 | A * | 6/1998 | Lowe | A61M 5/3205 206/364 |
| 5,967,778 | A * | 10/1999 | Riitano | A61C 19/002 206/366 |
| 6,026,959 | A * | 2/2000 | Lowe | A61M 5/3205 206/365 |
| 6,053,314 | A * | 4/2000 | Pittman | A61M 5/3205 206/366 |
| 6,315,113 | B1 * | 11/2001 | Britton | A61M 5/3202 204/275.1 |
| 6,637,587 | B2 * | 10/2003 | Britton | A61M 5/3278 206/210 |
| 7,119,689 | B2 * | 10/2006 | Mallett | B07C 7/005 209/583 |
| 8,926,489 | B2 * | 1/2015 | Brunson | A61M 5/3213 206/364 |
| 9,339,266 | B2 * | 5/2016 | Alcouloumre | A61B 17/06114 |

* cited by examiner

*Primary Examiner* — Nina Bhat

(57) ABSTRACT

This dissolvent is an inorganic compound of silica gel that is stabile and lasts for decades. Pleasant gold color, no evident odor or vapor, and it will not spill, or degrade over the decades, while awaiting use. After full and complete use with several syringes needles being dissolved at one location, these sharps will blacken and corrode and dissolve away, and the gel then becomes ordinary harmless waste to be conveniently discarded. This dissolvent gel will blunt sharp points and edges of sharps instantly to become totally useless. The useless sharps and needles will carry no infection, no living organism, no viruses, no pathogens, no bacterium, just nothing, just scrap! Nothing sharp or dangerous or infectious is left to be in the trash, or in the landfill, or in the ocean—it's just harmless scrap.

7 Claims, 25 Drawing Sheets

FIGURE 6

HAZARDOUS MEDICAL SHARPS & SYRINGES

| DISINFECTANT & DISPOSAL MEANS | MEDICAL ITEM | REFIT/STERILIZE FOR REUSE |
|---|---|---|
| Yes | Disposable Syringe | No |
| Needle | Specialty Syringes | Holder/Barrel |
| Yes | Butterfly Syringe | No |
| Entire Unit | Safety Syringes | No |
| Yes | Devices/Blood Services | No |
| Blades | Scalpel Blades | Handle |
| Yes | Suture Needles | No |
| Yes | Catheter Tips | No |
| Yes | Hemostats/Clamps | Partial Reuse |
| Yes | Stents | No |
| Yes | Pins/Nails | No |
| Blade | Saw Blades | Tool Reuse |
| Only Disposable Parts | Tools & Misc. Devices, & Instruments | Tools & Devices in Part |

MEDICALLY ASSISTED SENIORS

DISINFECTANT & DISPOSAL MEANS
FOR HAZARDOUS MEDICAL SHARPS & SYRINGES

CHEMICAL GEL TO DISSOLVE METAL AND HAZARDOUS MEDICAL SHARPS

U.S. PATENT REFERENCES

Of Note: As suggested and required in the MPEP that comments, evaluations, and such are to be included in the patent application. Such comments are to be included and kept available, as requisite, in the file wrapper to be available 'forever' for future issues. These comments are to ascertain that the inventor[s] have looked at the patents cited, and considered their value and effect upon their application, so as to be a guide for the claims made in their own current patent in application.

Thus, there is set in the left-hand margin, a code and measure of value, to represent a critique of the prior art as cited in this patent in application.

THE VALUES SO RECORDED ARE AS FOLLOWS

+++ of RELEVANCE, meaning that the cited patent in application has several features and components that are relevant in the prior art.

++ of RELATED values, meaning that this patent in application has a feature or component that can be construed as related in prior art.

+ of INTEREST only, wherein a feature is noted to be similar, but not the same, as in this patent in application.

x of no interest or value in this patent application.

U.S. PATENT REFERENCES

Of Note:

The following are Patent Classification Codes [Cl.Code] that are divided into Sections that are relevant to the Patent in Application herein. These Codes are general to the issues at hand in the following fields of endeavor, and as such are recorded in the left-hand margin for the cited Reference Patents in Prior Art. These Cl.Code[s] are numbered usually first to identify the Sections of the prior art, and are followed by the ratings of relevance as applicable to the patent in application.

| Cl. Code | Section Descriptions |
|---|---|
| 1. | Dissolvent & Etchant |
| 2. | Syringe to be Ground, Crushed & Destroyed, or Encapsulated |
| 3. | Containers for Sharps & Needles |
| 4. | Other Equipment: Scalpels, Stents, Catheters, Instrument Tips |
| 5. | Non-Metal Patents & Plastics |
| 6. | Syringes: Safety Types & Retracting Types |
| 7. | Needles Demounted & Removed |
| 8. | Bulk & Large Containers & Waste Systems |
| 9. | Chemical, Electrical, Microwave, inc. Steam & Freezing |
| 10. | Gel- All Types |

U.S. PATENTS

| | | | | |
|---|---|---|---|---|
| 10x | 585,365A | Jul. 29, 1897 | Skiffington | 165/108 |
| 10+ | 606,783A | Aug. 5, 1898 | Henderson | 202/185.1 |
| 10+ | 1,413,457A | Apr. 18, 1922 | Collins | 210/799 |
| 10+ | 1,674,558A | Jun. 19, 1928 | Miller | 34/424 |
| 10++ | 1,748,315A | Feb. 25, 1930 | Stoewener | 423/338 |
| 10++ | 1,751,955A | Mar. 25, 1930 | Stoewener | 423/339 |
| 10++ | 1,755,496A | Apr. 22, 1930 | Behrman | 423/330.1 |
| 10+ | 1,756,625A | Apr. 29, 1930 | Behrman | 502/60 |
| 10++ | 1,798,766A | Mar. 31, 1931 | Stoewener | 502/405 |
| 10x | 2,030,901A | Feb. 18, 1936 | Strain | 560/216 |
| 10++ | 2,114,123A | Apr. 12, 1938 | Heuser | 423/339 |
| 10+ | 2,213,211A | Sep. 3, 1940 | Fleckenstein et al | 106/421 |
| 10x | 2,302,297A | Nov. 17, 1942 | Connolly | 208/120.01 |
| 10x | 2,356,128A | Aug. 22, 1944 | Thomas et al | 525/332.6 |
| 10++ | 2,370,200 | Feb. 27, 1945 | Sliahaker | 422/129 |
| 10x | 2,383,921A | Aug. 28, 1945 | Soday | 585/439 |
| 10++ | 2,386,337A | Oct. 9, 1945 | Moyer | 423/335 |
| 1x | 2,441,396A | May 11, 1948 | Corwin et al | 534/586 |
| 10x | 2,470,361A | May 17, 1949 | Miller et al | 560/216 |
| 10+ | 2,483,868A | Oct. 4, 1949 | Archer et al | 423/338 |
| 10++ | 2,551,014A | May 1, 1951 | Kimberlin Jr. et al | 502/8 |
| 10++ | 2,601,235A | Jun. 24, 1952 | Alexander et al | 423/339 |
| 9+ | 2,719,123A | Sep. 27, 1955 | Merker | 508/203 |
| 10++ | 2,731,326A | Jan. 17, 1956 | Alexander et al | 423/338 |
| 10+++ | 2,763,533A | Sep. 18, 1956 | Ashley et al | 423/330.1 |
| 10+ | 2,858,255A | Oct. 28, 1958 | Segui et al | 202/219 |
| 3++ | 2,990,113A | Jun. 27, 1961 | Fosbrink et al | 232/7 |
| 10+++ | 3,047,507A | Jul. 31, 1962 | Winslow | 252/75 |
| 10+ | 3,190,740A | Jun. 22, 1965 | Fleming | 428/610 |
| 10x | 3,216,922A | Nov. 9, 1965 | O'Hara | 208/111.3 |
| 10+ | 3,250,594A | May 10, 1966 | Burke, Jr. et al | 423/339 |
| 3x | 3,343,709A | Sep. 26, 1967 | Henderson | 220/259.5 |
| 10++ | 3,445,189A | May 20, 1969 | Maat et al | 423/325 |
| 10++ | 3,782,982A | Jan. 1, 1974 | Pierson | 106/603 |
| 3x | 3,817,420A | Jun. 18, 1974 | Heisler | 220/60R |
| 3+ | 3,876,067A | Apr. 8, 1975 | Schwarz | 206/205 |
| 3,8x | 3,893,615A | Jul. 8, 1975 | Johnson | 232/43. |
| 9+ | 3,911,107A | Oct. 7, 1975 | Krezanoski | 424/78 |
| 10++ | 3,967,563A | Jul. 6, 1976 | Wason | 106/288B |
| 1,9+ | 3,976,500A | Aug. 24, 1976 | Fadgen Jr. | 134/2 |
| 10+++ | 4,067,746A | Jan. 10, 1978 | Wason et al | 106/288B |

| | | -continued | | |
|---|---|---|---|---|
| 1x | 4,087,359A | May 2, 1978 | Patron et al | 210/50 |
| 10+ | 4,103,742A | Aug. 1, 1978 | Swanson | 166/282 |
| 10| | 4,155,769A | May 22, 1979 | Almagro | 106/193J |
| 10+ | 4,205,724A | Jun. 3, 1980 | Swanson | 166/302 |
| 3+ | 4,232,784A | Nov. 11, 1980 | Hesselgren | 206/210 |
| 10++ | 4,244,826A | Jan. 13, 1981 | Swanson | 252/8.55C |
| 10+ | 4,272,509A | Jun. 9, 1981 | Wason | 424/49 |
| 5x | 4,291,084A | Sep. 22, 1981 | Segal | 428/212 |
| 10+ | 4,317,735A | Mar. 2, 1982 | Crowe | 252/8.55C |
| 2+ | 4,404,881A | Sep. 20, 1983 | Hanifl | 83/167 |
| 2,3+ | 4,410,086A | Oct. 18, 1983 | Simpson | 206/366 |
| 10+ | 4,422,880A | Dec. 27, 1983 | Wason et al | 106/288B |
| 2,4,3+ | 4,452,358A | Jun. 5, 1984 | Simpson | 206/366 |
| 10+ | 4,461,892A | Jul. 24, 1984 | Nishikawa et al | 536/65 |
| 3+ | 4,488,463A | Dec. 18, 1984 | Pepper | 206/366 |
| 3,2+ | 4,494,652A | Jan. 22, 1985 | Nelson et al | 206/366 |
| 10++ | 4,515,700A | May 7, 1985 | Hitzman | 252/8.55R |
| 9+ | 4,526,751A | Jul. 2, 1985 | Gartner | 422/37 |
| 2,3+ | 4,565,311A | Jan. 21, 1986 | Puliese et al | 225/94 |
| 2,3+ | 4,553,687A | Nov. 19, 1985 | Harkins et al | 225/93 |
| 3+ | D 282,009S | Dec. 31, 1985 | Gianni | D24/99 |
| 3x | D 282,722S | Feb. 25, 1986 | Lott | D9/435 |
| 10+ | 4,595,578A | Jun. 17, 1986 | Cohen et al | 423/338 |
| 8x | 4,614,752A | Sep. 30, 1986 | Fuchs | 521/44.5 |
| 10+ | 4,624,795A | Nov. 25, 1986 | Dawson et al | 252/8.553 |
| 3x | D 287,756S | Jan. 13, 1987 | Szablak et al | D24/99 |
| 3x | 4,657,139A | Apr. 14, 1987 | Hanift | 220/336 |
| 9x | 4,659,467A | Apr. 21, 1987 | Spearman | 210/282 |
| 3,9+ | 4,662,516A | May 5, 1987 | Baker Sr. et al | 206/363 |
| 9,3x | 4,663,122A | May 5, 1987 | Sparks | 422/26 |
| 6+ | 4,664,259A | May 12, 1987 | Landis | 206/365 |
| 10+ | 4,704,425A | Nov. 3, 1987 | Lagarde et al | 524/492 |
| 4,3+ | 4,714,168A | Dec. 22, 1987 | Johnson et al | 220/1T |
| 3+ | 4,715,498A | Dec. 29, 1987 | Hanifl | 206/366 |
| 1++ | 4,718,447A | Jan. 12, 1988 | Marshall | 137/268 |
| 3x | 4,744,614A | May 17, 1988 | Gombosi | 312/242 |
| 10++ | 4,765,818A | Aug. 23, 1988 | Che et al | 65/18.1 |
| 10x | 4,780,356A | Oct. 25, 1988 | Otouma et al | 428/212 |
| 10++ | 4,784,982A | Nov. 15, 1988 | Usui et al | 502/410 |
| 10++ | 4,806,665A | Feb. 21, 1989 | Jones et al | 556/413 |
| 3+ | 4,809,850A | Mar. 7, 1989 | Laible et al | 206/366 |
| 3,9++ | 4,816,307A | Mar. 28, 1989 | Honeycutt | 428/34.1 |
| 9x | 4,826,536A | May 2, 1989 | Raythatha et al | 106/465 |
| 3+ | 4,842,138A | Jun. 27, 1989 | Sandel et al | 206/370 |
| 1,9+ | 4,863,580A | Sep. 5, 1989 | Epner | 204/269 |
| 3,6+ | 4,865,813A | Sep. 12, 1989 | Leon | 422/101 |
| 6+ | 4,886,497A | Dec. 12, 1989 | Scholl Jr. | 604/111 |
| 7,6x | 4,904,244A | Feb. 27, 1990 | Harsh et al | 604/187 |
| 2,8,9+ | 4,905,916A | Mar. 6, 1990 | Sorwick et al | 241/23 |
| 3,8+ | 4,911,294A | Mar. 27, 1990 | Russo et al | 206/366 |
| 6++ | 4,915,698A | Apr. 10, 1990 | Levenson | 604/192 |
| 10+ | 4,915,870A | Apr. 10, 1990 | Jones | 252/313.2 |
| 10x | 4,915,923A | Apr. 10, 1990 | Ogawa et al | 423/335 |
| 3+ | 4,919,264A | Apr. 24, 1990 | Shinall | 206/210 |
| 3+ | 4,919,569A | Apr. 24, 1990 | Wittenzelliner | 405/128 |
| 8,9x | 4,925,532A | May 15, 1990 | Meuser el al | 202/219 |
| 3+ | 4,927,076A | May 22, 1990 | Simpson | 229/132 |
| 3,9++ | 4,936,449A | Jun. 26, 1990 | Conard et al | 206/366 |
| 3x | 4,940,157A | Jul. 10, 1990 | Inagaki | 220/254 |
| 1x | 4,950,408A | Aug. 21, 1990 | Duisters et al | 210/660 |
| 10x | 4,954,220A | Sep. 4, 1990 | Rushmere | 162/168.3 |
| 10+ | 4,956,167A | Sep. 11, 1990 | Aldcroft et al | 423/339 |
| 9,1+ | 4,960,500A | Oct. 2, 1990 | Epner | 204/269 |
| 2,3+ | 4,961,541A | Oct. 9, 1990 | Hashimoto | 241/65 |
| 3+ | 4,979,616A | Dec. 25, 1990 | Clanton | 206/364 |
| 3,7+ | 4,989,307A | Feb. 5, 1991 | Sharpe et al | 29/240 |
| 10+ | 4,989,794A | Feb. 5, 1991 | Askew et al | 241/16 |
| 10+ | 4,992,251A | Feb. 12, 1991 | Aldcroft et al | 423/335 |
| 3,8+ | 5,003,892A | Apr. 2, 1991 | Bricken | 110/346 |
| 3+ | 5,031,767A | Jul. 16, 1991 | Bruno | 206/370 |
| 3,2,10+ | 5,038,929A | Aug. 13, 1991 | Kubofcik | 206/210 |
| 3+ | 5,039,004A | Aug. 13, 1991 | Simpson | 229/132 |
| 3+ | 5,046,613A | Sep. 10, 1991 | Baudry et al | 206/366 |
| 2,8,9x | 5,046,669A | Sep. 10, 1991 | Wallace et al | 241/23 |
| 1x | 5,047,224A | Sep. 10, 1991 | Dhooge | 423/437 |
| 8x | 5,054,696A | Oct. 8, 1991 | Mennel et al | 241/34 |
| 8x | 5,064,124A | Nov. 12, 1991 | Chang | 241/33 |
| 7x | 5,067,223A | Nov. 26, 1991 | Bruno | 29/426.5 |
| 3+ | 5,076,429A | Dec. 31, 1991 | Patrick et al | 206/370 |

| | | -continued | | |
|---|---|---|---|---|
| 3++ | 5,080,251A | Jan. 14, 1992 | Noack | 220/335 |
| 1x | 5,082,492A | Jan. 21, 1992 | Gallup et al | 75/712 |
| 3,6,2+ | 5,084,027A | Jan. 28, 1992 | Bernard | 604/192 |
| 3,7+ | 5,086,922A | Feb. 11, 1992 | Sagstetter et al | 206/366 |
| 2,3,9+ | 5,091,621A | Feb. 25, 1992 | Butler | 219/68 |
| 2,3+ | 5,092,462A | Mar. 3, 1992 | Sagstetter et al | 206/366 |
| 10x | 5,098,965A | Mar. 24, 1992 | Bauer et al | 525/507 |
| 2,9,5+ | 5,106,594A | Apr. 21, 1992 | Held et al | 422/292 |
| 3+ | 5,107,990A | Apr. 28, 1992 | Wicherski et al | 206/366 |
| 1++ | 5,116,415 | May 26, 1992 | Rinehart | 75/711 |
| 9,5++ | 5,120,409A | Jun. 9, 1992 | Hanulik | 204/105R |
| 3,2x | 5,124,126A | Jun. 23, 1992 | Ripp | 422/26 |
| 3,5x | 5,148,940A | Sep. 22, 1992 | Mendise | 220/404 |
| 3+ | 5,163,375A | Nov. 17, 1992 | Withers et al | 110/346 |
| 9+ | 5,166,488A | Nov. 24, 1992 | Peppard | 219/10.55R |
| 3x | 5,167,193A | Dec. 1, 1992 | Withers et al | 110/346 |
| 8,3+ | 5,168,612A | Dec. 8, 1992 | Schultz et al | 29/33R |
| 3x | 5,183,156A | Feb. 2, 1993 | Bruno | 206/366 |
| 2,3x | 5,186,402A | Feb. 16, 1993 | Lin | 241/55 |
| 6x | 5,188,601A | Feb. 23, 1993 | King | 604/110 |
| 3+ | 5,201,417A | Apr. 13, 1993 | Outlaw, III | 206/366 |
| 3x | 5,205,409A | Apr. 27, 1993 | Bruno | 206/370 |
| 7,6+ | 5,205,833A | Apr. 27, 1993 | Harsh et al | 604/240 |
| 9+ | 5,212,362A | May 18, 1993 | Burden et al | 219/69.1 |
| 8x | 5,217,688A | Jun. 8, 1993 | Von Lersner | 422/26 |
| 9x | 5,219,660A | Jun. 15, 1993 | Wason et al | 428/403 |
| 6,8+ | 5,224,596A | Jul. 6, 1993 | Kruger | 206/366 |
| 3+ | 5,230,426A | Jul. 27, 1993 | Keefe et al | 206/205 |
| 10+ | 5,230,833A | Jul. 27, 1993 | Romberger et al | 252/363.5 |
| 5,8x | 5,235,795A | Aug. 17, 1993 | DeBusk | 53/467 |
| 9x | 5,236,352A | Aug. 17, 1993 | Carpenter | 432/13 |
| 10++ | 5,236,683A | Aug. 17, 1993 | Nakazawa et al | 423/335 |
| 3+ | 5,240,108A | Aug. 31, 1993 | Tonna | 206/366 |
| 7,6+ | 5,242,401A | Sep. 7, 1993 | Colsky | 604/110 |
| 9+ | 5,248,486A | Sep. 28, 1993 | Matsuoka et al | 424/294 |
| 3+ | 5,249,679A | Oct. 5, 1993 | Dondlinger | 206/366 |
| 2,9x | 5,264,675A | Nov. 23, 1993 | Butler | 219/68 |
| 3+ | 5,265,724A | Nov. 30, 1993 | Dondlinger | 206/366 |
| 3,2,9| | 5,268,549A | Dec. 7, 1993 | Butler | 219/68 |
| 3,9++ | 5,271,892A | Dec. 21, 1993 | Hanson et al | 422/25 |
| 3,7,9+ | 5,277,868A | Jan. 11, 1994 | Langford | 422/21 |
| 3+ | 5,281,391A | Jan. 25, 1994 | Hanson et al | 422/25 |
| 8,2+ | 5,287,609A | Feb. 22, 1994 | Chang | 29/33R |
| 3,9++ | 5,288,964A | Feb. 22, 1994 | Walker et al | 219/68 |
| 9+ | 5,304,713A | Apr. 19, 1994 | Tanaka et al | 588/258 |
| 6+ | 5,311,985A | May 17, 1994 | Suida | 206/210 |
| 6x | 5,312,348A | May 17, 1994 | Sans | 604/110 |
| 10+ | 5,318,833A | Jun. 7, 1994 | Fujimoto et al | 428/304.4 |
| 3+ | 5,323,901A | Jun. 28, 1994 | Outlaw, III | 206/366 |
| 2,9+ | 5,329,087A | Jul. 12, 1994 | Kohl et al | 219/68 |
| 7,2+ | 5,340,039A | Aug. 23, 1994 | Lefevre | 241/84 |
| 10+ | 5,342,876A | Aug. 30, 1994 | Abe et al | 524/493 |
| 6x | 5,346,474A | Sep. 13, 1994 | King | 604/110 |
| 8,9++ | 5,348,235A | Sep. 20, 1994 | Pappas | 241/41 |
| 9x | 5,352,271A | Oct. 4, 1994 | Margaria et al | 75/526 |
| 2+ | 5,354,000A | Oct. 11, 1994 | Wright et al | 241/33 |
| 8x | 5,360,594A | Nov. 1, 1994 | Meijer | 422/37 |
| 8,2,9+ | 5,362,443A | Nov. 8, 1994 | Tanaka et al | 422/26 |
| 9+ | 5,370,869A | Dec. 6, 1994 | Shanbrom | 424/78.22 |
| 3,8+ | 5,372,252A | Dec. 13, 1994 | Alexander | 206/210 |
| 10x | 5,372,884A | Dec. 13, 1994 | Abe et al | 428/331 |
| 9,3 | 5,391,849A | Feb. 21, 1995 | Furuya et al | 219/68 |
| 2,8,5+ | 5,397,068A | Mar. 14, 1995 | Solomons | 241/100 |
| 2+ | 5,401,444A | Mar. 28, 1995 | Spinello | 264/0.5 |
| 10x | 5,403,955A | Apr. 4, 1995 | Farooq | 564/15 |
| 4,3,6+ | 5,411,193A | May 2, 1995 | Culp | 224/252 |
| 3,9++ | 5,413,757A | May 9, 1995 | Kutner et al | 422/21 |
| 3+ | 5,415,315A | May 16, 1995 | Ramirez | 220/346 |
| 10+ | 5,417,977A | May 23, 1995 | Honeycutt | 424/443 |
| 10++ | 5,419,888A | May 30, 1995 | McGill et al | 423/338 |
| 2,8 | 5,429,315A | Jul. 4, 1995 | Wollert et al | 241/100 |
| 3x | 5,431,276A | Jul. 11, 1995 | Lialin | 206/222 |
| 8x | 5,433,412A | Jul. 18, 1995 | Watt et al | 206/370 |
| 9,6| | 5,437,656A | Aug. 1, 1995 | Shikani et al | 604/89.1 |
| 1,3,9,4+++ | 5,441,622A | Aug. 15, 1995 | Langford | 204/275 |
| 1,9,3+++ | 5,441,623A | Aug. 15, 1995 | Langford | 204/275 |
| 8,2+ | 5,447,685A | Sep. 5, 1995 | Sievert et al | 422/22 |
| 9x | 5,449,438A | Sep. 12, 1995 | Jagau et al | 201/10 |
| 10x | 5,468,475A | Nov. 21, 1995 | Shaku et al | 424/70.16 |

-continued

| | | | | |
|---|---|---|---|---|
| 2,3,9x | 5,468,928A | Nov. 21, 1995 | Yelvington | 219/68 |
| 8x | 5,470,022A | Nov. 28, 1995 | Wright et al | 241/33 |
| 9x | 5,481,064A | Jan. 2, 1996 | Kato et al | 588/205 |
| 6,9x | 5,482,038A | Jan. 9, 1996 | Ruff | 128/642 |
| 7,3,9++ | 5,482,207A | Jan. 9, 1996 | Nelson et al | 232/43.2 |
| 3+ | 5,494,158A | Feb. 27, 1996 | Erickson | 206/366 |
| 3x | 5,495,941A | Mar. 5, 1996 | Leonard | 206/366 |
| 10++ | 5,503,820A | Apr. 2, 1996 | Moffett et al | 423/333 |
| 5,9x | 5,508,004A | Apr. 16, 1996 | Held et al | 422/22 |
| 1+ | 5,512,201A | Apr. 30, 1996 | Singh et al | 252/142 |
| 10+ | 5,512,271A | Apr. 30, 1996 | McKeown et al | 424/49 |
| 8x | 5,513,804A | May 7, 1996 | Keeler et al | 241/16 |
| 3+ | 5,570,783A | Nov. 5, 1996 | Thorne et al | 206/366 |
| 8,9x | 5,570,845A | Nov. 5, 1996 | Lewis et al | 241/21 |
| 1+ | 5,573,652A | Nov. 12, 1996 | Klyama et al | 205/98 |
| 8x | 5,582,793A | Dec. 10, 1996 | Glazer et al | 422/26 |
| 10++ | 5,589,150A | Dec. 31, 1996 | Kano et al | 423/338 |
| 9+ | 5,591,350A | Jan. 7, 1997 | Piechocki et al | 210/764 |
| 10x | 5,601,699A | Feb. 11, 1997 | Degnan et al | 208/114 |
| 3x | 5,609,837A | Mar. 11, 1997 | Russell et al | 422/102 |
| 3,6x | 5,611,429A | Mar. 18, 1997 | Phillips | 206/365 |
| 10+ | 5,612,281A | Mar. 18, 1997 | Kobayashi et al | 503/227 |
| 8,9x | 5,615,627A | Apr. 1, 1997 | Marr, Jr. | 110/346 |
| 9x | 5,628,261A | May 13, 1997 | Beckstead et al | 110/346 |
| 3x | 5,631,166A | May 20, 1997 | Jewell | 436/45 |
| 10+ | 5,635,196A | Jun. 3, 1997 | Murphy | 424/409 |
| 2,8x | 5,639,031A | Jun. 17, 1997 | Wright et al | 241/33 |
| 2,8x | 5,662,281A | Sep. 2, 1997 | Wollert et al | 241/100 |
| 10x | 5,674,175A | Oct. 7, 1997 | Bailey | 588/255 |
| 8,9++ | 5,676,070A | Oct. 14, 1997 | Maganas et al | 110/245 |
| 9,3+ | 5,686,045A | Nov. 11, 1997 | Carter | 422/20 |
| 3+ | 5,687,839A | Nov. 18, 1997 | Gnau III et al | 206/204 |
| 2,8,9x | 5,692,687A | Dec. 2, 1997 | Kateley | 241/65 |
| 9x | 5,709,842A | Jan. 20, 1998 | Held et al | 422/292 |
| 2,3,9+ | 5,741,230A | Apr. 21, 1998 | Miller | 604/110 |
| 1,3,10+++ | 5,749,376A | May 12, 1998 | Wilk et al | 128/898 |
| 3+ | 5,758,775A | Jun. 2, 1998 | Lowe | 206/571 |
| 2,3,9+ | 5,761,975A | Jun. 9, 1998 | Waluda | 82/58 |
| 10+ | 5,783,489A | Jul. 21, 1998 | Kaufman et al | 438/692 |
| 10x | 5,795,916A | Aug. 18, 1998 | Sekine et al | 514/567 |
| 8,9x | 5,799,883A | Sep. 1, 1998 | Lewis et al | 241/21 |
| 4,3+ | 5,807,230A | Sep. 15, 1998 | Argenta et al | 588/258 |
| 9x | 5,830,419A | Nov. 3, 1998 | Held et al | 422/307 |
| 9x | 5,833,922A | Nov. 10, 1998 | Held et al | 422/22 |
| 10++ | 5,843,743A | Dec. 1, 1998 | Hubbell et al | 435/177 |
| 9x | 5,852,062A | Dec. 22, 1998 | Carpenter | 521/41 |
| 5,10+ | 5,871,867A | Feb. 16, 1999 | Rausch et al | 429/247 |
| 10x | 5,882,388A | Mar. 16, 1999 | Adair et al | 106/31.6 |
| 10x | 5,885,638A | Mar. 23, 1999 | Takayanagi et al | 426/271 |
| 2,3+ | 5,887,807A | Mar. 30, 1999 | Beinecke | 241/36 |
| 6x | 5,894,015A | Apr. 13, 1999 | Rechtin | 422/301 |
| 3++ | 5,947,285A | Sep. 7, 1999 | Gaba et al | 206/366 |
| 10x | 5,965,244A | Oct. 12, 1999 | Tang et al | 428/195 |
| 9+ | 5,976,988A | Nov. 2, 1999 | Konuma et al | 438/745 |
| 2,3,9+ | 5,979,275A | Nov. 9, 1999 | Waluda | 82/58 |
| 10+ | 5,998,329A | Dec. 7, 1999 | Derolf et al | 502/407 |
| 8,3x | 6,027,490A | Feb. 22, 2000 | Radford et al | 604/540 |
| 2,3+ | 6,036,671A | Mar. 14, 2000 | Frey | 604/110 |
| 4+ | 6,077,290A | Jun. 20, 2000 | Marini | 606/205 |
| 10,9+ | 6,110,439A | Aug. 29, 2000 | Deshpande et al | 423/338 |
| 3,9+ | 6,142,303A | Nov. 7, 2000 | Dendy et al | 206/568 |
| 2,3+ | 6,158,314A | Dec. 12, 2000 | Thead et al | 83/23 |
| 10x | 6,165,351A | Dec. 26, 2000 | Laine et al | 208/118 |
| 10x | 6,187,430A | Feb. 13, 2001 | Mukoyoshi et al | 428/331 |
| 10,9+ | 6,203,484A | May 20, 2001 | Lepore et al | 588/255 |
| 8,9x | 6,248,985B1 | Jun. 19, 2001 | Tomascello | 219/679 |
| 1+ | 6,258,294B1 | Jul. 10, 2001 | Johnson II et al | 252/79.3 |
| 8,9x | 6,262,405B1 | Jul. 17, 2001 | Wicks et al | 219/679 |
| 2,3,1+++ | 6,315,113B1 | Nov. 13, 2001 | Britton et al | 206/210 |
| 3,2+ | 6,332,534B1 | Dec. 25, 2001 | Hammett | 206/366 |
| 2,9+ | 6,337,454B1 | Jan. 8, 2002 | Walker | 219/68 |
| 8,9x | 6,344,638B1 | Feb. 5, 2002 | Tomascello | 219/770 |
| 1,9+ | 6,346,221B1 | Feb. 12, 2002 | Wagner | 422/184.1 |
| 6,3+ | 6,348,044B1 | Feb. 19, 2002 | Coletti et al | 604/192 |
| 5x | 6,348,540B1 | Feb. 19, 2002 | Sugioka et al | 524/577 |
| 8,2x | 6,357,682B1 | Mar. 19, 2002 | Hext | 241/161 |
| 10++ | 6,375,914B1 | Apr. 23, 2002 | Vangbo | 423/338 |
| 10++ | 6,380,265B1 | Apr. 30, 2002 | Pryor et al | 516/85 |
| 10x | 6,403,059B1 | Jun. 11, 2002 | Martin et al | 424/49 |

-continued

| | | | | |
|---|---|---|---|---|
| 10x | 6,419,174B1 | Jul. 16, 2002 | McGill et al | 242/49 |
| 10+ | 6,438,867B1 | Aug. 27, 2002 | Teich et al | 34/470 |
| 1,3+ | 6,444,174B1 | Sep. 3, 2002 | Lascombes | 422/102 |
| 3x | 6,488,675B1 | Dec. 3, 2002 | Radford et al | 604/540 |
| 10,9+ | 6,500,870B1 | Dec. 31, 2002 | Linsten et al | 516/81 |
| 3x | 6,527,115B2 | Mar. 4, 2003 | Rabiner et al | 206/363 |
| 8x | D 478,701S | Aug. 19, 2003 | Panek Jr. | D34/25 |
| 1,2,3+++ | 6,637,587B2 | Oct. 28, 2003 | Britton | 206/210 |
| 6,3+ | 6,659,277B2 | Dec. 9, 2003 | Coletti et al | 206/365 |
| 10x | 6,689,437B1 | Feb. 10, 2004 | Ubara et al | 428/35.7 |
| 5x | 6,828,010B2 | Dec. 7, 2004 | Kubota et al | 428/213 |
| 3x | 6,859,005B2 | Feb. 22, 2005 | Boliver | 318/480 |
| 10+ | 6,872,765B1 | Mar. 29, 2005 | Betz et al | 524/261 |
| 10,9++ | 6,884,822B2 | Apr. 26, 2005 | Wang et al | 516/111 |
| 1x | 6,896,808B1 | May 24, 2005 | Jay | 210/638 |
| 10x | 6,905,778B2 | Jun. 14, 2005 | Tullos et al | 428/480 |
| 5x | 6,919,129B2 | Jul. 19, 2005 | Longmoore | 428/343 |
| 6,7x | 6,929,126B1 | Aug. 16, 2005 | Herbert | 206/365 |
| 2,3++ | 6,969,374B2 | Nov. 29, 2005 | Krantz et al | 604/240 |
| 10x | 6,969,692B2 | Nov. 29, 2005 | Brady et al | 502/66 |
| 8x | 7,114,629B2 | Oct. 3, 2006 | Panek, Jr. | 220/345.1 |
| 8x | 7,119,689B2 | Oct. 10, 2006 | Mallett et al | 340/572.1 |
| 10+ | 7,125,432B2 | Oct. 24, 2006 | Huang | 51/308 |
| 3x | 7,159,714B2 | Jan. 9, 2007 | Wilkinson et al | 206/366 |
| 8x | D 542,999S | May 15, 2007 | Japuntich et al | D34/27 |
| 8x | 7,275,645B2 | Oct. 2, 2007 | Mallett et al | 209/702 |
| 1,9+ | 7,294,409B2 | Nov. 13, 2007 | Lye et al | 428/610 |
| 8x | 7,296,688B2 | Nov. 20, 2007 | Mallett et al | 209/702 |
| 8x | 7,303,081B2 | Dec. 4, 2007 | Mallett et al | 209/702 |
| 8x | 7,341,147B2 | Mar. 11, 2008 | Mallett et al | 206/364 |
| 2x | 7,360,730B2 | Apr. 22, 2008 | Brown | 241/92 |
| 8x | 7,364,049B2 | Apr. 29, 2008 | Panek, Jr. | 220/345.1 |
| 8+ | 7,533,028B2 | May 12, 2009 | Mallett et al | 705/1 |
| 8x | 7,533,029B2 | May 12, 2009 | Mallett et al | 705/1 |
| 10+ | 7,553,416B2 | Jun. 30, 2009 | Hua et al | 210/500.1 |
| 8x | 7,562,025B2 | Jul. 14, 2009 | Mallett et al | 705/1 |
| 8x | 7,565,299B2 | Jul. 21, 2009 | Mallett et al | 705/1 |
| 3+ | 7,596,844B2 | Oct. 6, 2009 | Japuntich et al | 29/402.01 |
| 8x | 7,620,559B2 | Nov. 17, 2009 | Mallett et al | 705/1 |
| 2x | 7,748,654B2 | Jul. 6, 2010 | Brown | 241/30 |
| 1+ | 7,772,451B2 | Aug. 10, 2010 | Enda et al | 588/319 |
| 6x | 7,775,357B2 | Aug. 17, 2010 | Clarke | 206/365 |
| 8x | 7,784,167B2 | Aug. 31, 2010 | Panek, Jr. | 29/527.1 |
| 10++ | 7,803,343B2 | Sep. 28, 2010 | Hua et al | 423/338 |
| 10+ | 7,824,665B2 | Nov. 2, 2010 | Miyamoto et al | 424/70.13 |
| 8,9x | 7,898,201B2 | Mar. 1, 2011 | Fisher et al | 318/466 |
| 6x | 7,998,106B2 | Aug. 16, 2011 | Thome, Jr. et al | 604/32 |
| 3,4x | 8,162,139B2 | Apr. 24, 2012 | Iske et al | 206/365 |
| 6x | 8,167,837B2 | May 1, 2012 | Judd et al | 604/110 |
| 8x | 8,167,858B2 | May 1, 2012 | Radford et al | 604/321 |
| 3,4x | 8,172,104B2 | May 8, 2012 | Weber | 220/62 |
| 8x | 8,195,328B2 | Jun. 5, 2012 | Mallett et al | 700/236 |
| 2,3+ | 8,201,323B2 | Jun. 19, 2012 | Miller et al | 29/801 |
| 8x | 8,201,704B2 | Jun. 19, 2012 | Finnestad et al | 220/23.86 |
| 8x | 8,204,620B2 | Jun. 19, 2012 | Mallett et al | 700/236 |
| 9x | 8,283,512B1 | Oct. 9, 2012 | Maganas | 588/313 |
| 3x | 8,333,292B2 | Dec. 18, 2012 | Finnestad | 220/254.9 |
| 3+++ | 8,393,488B2 | Mar. 12, 2013 | Japuntich et al | 220/254.1 |
| 3x | 8,393,489B1 | Mar. 12, 2013 | Stravitz | 220/264 |
| 3++ | 8,397,933B2 | Mar. 19, 2013 | Finnestad | 220/254.3 |
| 8,9x | 8,425,857B2 | Apr. 23, 2013 | Glazer et al | 422/292 |
| 6x | 8,448,785B2 | May 28, 2013 | Clarke | 206/365 |
| 3x | 8,460,250B2 | Jun. 11, 2013 | Imai | 604/220 |
| 3++ | 8,505,769B2 | Aug. 13, 2013 | Finnestad | 220/908 |
| 8,9x | 8,512,215B2 | Aug. 20, 2013 | Maganas | 588/249.5 |
| 3+ | 8,584,885B2 | Nov. 19, 2013 | Finnestad et al | 220/254.3 |
| 8+ | 8,613,366B2 | Dec. 24, 2013 | Finnestad et al | 220/345.1 |
| 8,9x | 8,652,404B2 | Feb. 18, 2014 | Glazer et al | 422/28 |
| 3,4x | 8,690,752B2 | Apr. 8, 2014 | Jose | 600/33 |
| 3,8,x | 8,695,834B2 | Apr. 15, 2014 | Panek, Jr. | 220/345.1 |
| 1,9+ | 8,702,838B2 | Apr. 22, 2014 | Shimomura et al | 75/710 |
| 3+ | 8,727,162B2 | May 20, 2014 | Finnestad | 220/254.3 |
| 3+ | 8,727,166B2 | May 20, 2014 | Finnestad | 220/254.9 |
| 3+ | 8,813,986B2 | Aug. 26, 2014 | Liscio et al | 220/211 |
| 1,9+ | 8,865,471B2 | Oct. 21, 2014 | Kinoshiro et al | 436/78 |
| Ix | 8,887,664B2 | Nov. 18, 2014 | Teichert | 118/712 |
| 10+ | 8,889,301B2 | Nov. 18, 2014 | Balsara et al | 429/300 |
| 10x | 8,900,623B2 | Dec. 2, 2014 | Lee | 424/439 |
| 6x | 8,936,570B2 | Jan. 20, 2015 | Choi | 604/110 |

-continued

| | | | | |
|---|---|---|---|---|
| 1++ | 8,946,015B2 | Feb. 3, 2015 | Duong et al | 438/197 |
| 10,9+ | 8,961,738B2 | Feb. 24, 2015 | Barinov et al | 156/712 |
| 1+ | 8,968,698B2 | Mar. 3, 2015 | Bednarski et al | 423/658.5 |
| 1++ | 8,974,572B2 | Mar. 10, 2015 | Uchara | 75/744 |
| 1++ | 8,979,974B2 | Mar. 17, 2015 | Nomura et al | 75/364 |

U.S. PATENTS IN APPLICATION

| | | | | |
|---|---|---|---|---|
| 8,9+ | 2014/0234165A1 | Aug. 21, 2014 | Glazer et al | 422/38 |
| 3,9+ | 2014/0166624A1 | Jun. 19, 2014 | Butler | 219/68 |
| 2,3,9+ | 2013/0334175A1 | Dec. 19, 2013 | Jackson et al | 219/68 |
| 10+ | 2013/0292839A1 | Nov. 7, 2013 | Fukami et al | 257/773 |
| 3,8x | 2013/0248395A1 | Sep. 26, 2013 | Guthrie | 206/365 |
| 8x | 2013/0113171A1 | May 9, 2013 | Pennings et al | 280/47.34 |
| 3+ | 2013/0019567A1 | Jan. 24, 2013 | Sandel et al | 53/428 |
| 3x | 2012/0260416A1 | Oct. 18, 2012 | Radford et al | 4/479 |
| 3+ | 2012/0037628A1 | Feb. 16, 2012 | Finnestad | 220/254.3 |
| 3+ | 2012/0037627A1 | Feb. 16, 2012 | Fnnestrad | 220/254.1 |
| 3+ | 2012/0037626A1 | Feb. 16, 2012 | Finnestad | 220/212 |
| 8,9++ | 2011/0268606A1 | Nov. 3, 2011 | Glazer et al | 422/22 |
| 3+ | 2011/0253716A1 | Oct. 20, 2011 | Japuntich et al | 220/254.3 |
| 3+ | 2010/0282623A1 | Nov. 11, 2010 | Reshamwala | 206/210 |
| 6,3+ | 2010/0276319A1 | Nov. 4, 2010 | Clarke | 206/365 |
| 3+ | 2010/0122925A1 | May 20, 2010 | Charbonneau et al | 206/370 |
| 3x | 2010/0108675A1 | May 6, 2010 | Meissen et al | 220/254.3 |
| 8x | 2010/0082459A1 | Apr. 1, 2010 | Tusa et al | 705/28 |
| 3+ | 2010/0069699A1 | Mar. 18, 2010 | Weber | 588/249.5 |
| 6,3+ | 2009/0255838A1 | Oct. 15, 2009 | Clarke | 206/365 |
| 8,9+ | 2009/0242674A1 | Oct. 1, 2009 | Lee et al | 241/65 |
| 8x | 2009/0145901A1 | Jun. 11, 2009 | Finnestad et al | 220/254.9 |
| 3+ | 2008/0217332A1 | Sep. 11, 2008 | Kleyman et al | 220/211 |
| 3,8x | 2008/0199299A1 | Aug. 21, 2008 | Baader et al | 414/811 |
| 2,3+ | 2008/0191071A1 | Aug. 14, 2008 | Brown | 241/29 |
| 3x | 2008/0190924A1 | Aug. 14, 2008 | Bobrov et al | 220/62.22 |
| 3,8x | 2008/0157434A1 | Jul. 3, 2008 | Panek | 264/297.1 |
| 3x | 2008/0156818A1 | Jul. 3, 2008 | Panek | 220/737 |
| 3,8x | 2008/0156666A1 | Jul. 3, 2008 | Panek | 206/1.5 |
| 3x | 2007/0027432A1 | Feb. 1, 2007 | Radford et al | 604/317 |
| 8x | 2006/0218002A1 | Sep. 28, 2006 | Mallett et al | 705/1 |
| 2,3+ | 2006/0014996A1 | Jan. 19, 2006 | Brown | 588/249.5 |
| 1,9++ | 2005/0287677A1 | Dec. 29, 2005 | Bosmann et al | 436/163 |
| 8x | 2005/0218142A1 | Oct. 6, 2005 | Finnestad et al | 220/264 |
| 3,9++ | 2005/0072758A1 | Apr. 7, 2005 | Jackson et al | 219/68 |
| 3,8x | 2004/0222335A1 | Nov. 11, 2004 | Panek, Jr. | 248/129 |
| 6x | 2004/0064108A1 | Apr. 1, 2004 | Krantz et al | 604/240 |
| 3+ | 2003/0213714A1 | Nov. 20, 2003 | Moats et al | 206/366 |
| 3,8x | 2002/0158068A1 | Oct. 31, 2002 | Panek, Jr. | 220/23.87 |
| 9,8+ | 2002/0145063A1 | Oct. 10, 2002 | Mosenson et al | 241/36 |
| 6x | 2002/0117412A1 | Aug. 29, 2002 | Rabiner et al | 206/363 |
| 6+ | 2002/0115987A1 | Aug. 22, 2002 | Hildwein et al | 606/1 |

WORLD PATENTS

Of Note: These Patents are referenced from the 'Relevant & Related' cited U. S. Patents.

| | |
|---|---|
| AU 538037 | February 1984 |
| CA 0526590 | June 1956 |
| CA 0584727 | October 1959 |
| CA 0951456 | July 1974 |
| CA 1189681 | February 1985 |

-continued

| | |
|---|---|
| CA 1183672 | December 1985 |
| DE 546465 | March 1932 |
| DE 1467019 | January 1969 |
| DE 1667078 | May 1971 |
| DE 2446038 | March 1987 |
| DE 0270289 | July 1989 |
| DE 29614563 | October 1996 |
| EP 0038172 | October 1981 |
| EP O120301 A2 | October 1984 |
| EP 0139754 | May 1985 |
| EP 0143848 | June 1985 |
| EP 0227334 | July 1987 |
| EP 236070 | September 1987 |
| EP 0257611 | March 1988 |
| EP 0301783 A2 | February 1989 |
| EP 0359552 | March 1990 |
| EP 0440962 | August 1991 |
| EP 0464289 | January 1992 |
| EP 0494599 | July 1992 |
| EP 0506033 | September 1992 |
| EP 0355045 B1 | May 1995 |
| EP 0978304A2 | February 2000 |
| FR 2687320 | August 1993 |
| JP 46-038603 | April 1971 |
| JP 47-35676 | September 1972 |
| JP 52-032899 | August 1977 |
| JP 53-65295 | June 1978 |
| JP 54-9588 | May 1979 |
| JP 0141818 | August 1982 |
| JP 57-055454 | November 1982 |
| JP 59-30730 | February 1984 |
| JP 61-010019 | January 1986 |
| JP 61-168520 | July 1986 |
| JP 61-186216 | August 1986 |
| JP 6214781 | January 1987 |
| JP 2113713 | May 1987 |
| JP 62-275014 | November 1987 |
| JP 0062362 | March 1989 |
| JP 0274515 | March 1990 |
| JP 0296711 | December 1990 |
| JP 04015237 | January 1992 |
| JP 041796 | February 1994 |
| UK 827586 | February 1960 |
| UK 883863 | December 1960 |
| UK 1044019 | September 1966 |
| UK 1094798 | December 1967 |
| UK 1186706 | April 1970 |
| UK 1264292 | February 1972 |
| UK 1300946 | December 1972 |
| UK 1416138 | December 1975 |
| UK 1447663 | August 1976 |
| UK 1482354 | August 1977 |
| UK 1482355 | August 1977 |
| UK 1501905 | February 1978 |
| UK 1532398 | November 1978 |
| UK 2018266 | October 1979 |
| UK 2038303 | December 1979 |
| UK 2038303 | July 1980 |
| UK 1265550 | March 1982 |
| UK 2146317 | April 1985 |
| UK 424246 | November 1993 |
| UK 2269377 | February 1994 |
| USSR 1178482 | September 1985 |
| WO 8803813 | June 1988 |
| WO 9007348 | July 1990 |
| WO 90/03330 | April 1990 |
| WO 91/07350 | May 1991 |
| WO 95/15771 | June 1995 |
| WO 97/34476 | September 1997 |

-continued

| WO/PCT/US/02707 | June 2002 |
| WO 09/02662 | December 2008 |
| WO 09/02663 | December 2008 |

REFERENCE SOURCE TEXTS

Iler, Ralph K. "The Chemistry of Silica: Solubility, Polymerization, Colloid, and Surface Properties, and Biochemistry" John Wiley & Sons, A Wiley-Interscience Publication, New York, 1979.
Ch. 3: "Polymerization of Silica", pp. 172-227;
Ch 4: "Colloidal Silica-Concentrated Sols", pp. 312-462;
Ch. 5: "Silica Gels & Powders", pp. 462-621.
Brauer, Georg, as Editor, & Strecher, Paul G., as Translation Editor of original German text of Stuttgart, Germany, 1962, "Handbook of Preparative Inorganic Chemistry" Academic Press, New York, 1965.
Part III, "Special Compounds", Section 1, "Adsorbents and Catalysts", authored by R. Wagner, pp. 1646-56.

BY APPENDIX ATTACHED

A. SILICA POWDER TESTING RESULTS;
B. SILICA GELS TESTING RESULTS; &
C. SILICA POWDER & GEL MIXTURE TESTING RESULTS.

FIELD OF SEARCH

The field of search involves the inorganic chemistry that controls and forms gels and gelled solutions. Am available candidate is in the silica family of silicon compounds that in part form glass. The colloidal silica and the like will combine with acids and salts in some cases to mix up a good reliable gel solution that is viscous enough to remain in place while dissolving the metal sharps concerned herein.

The organic combinations useful with an acidic chemical solution can be found, but they are not as stable and long-lasting as the inorganic materials.

Mixing of the chemical solutions into a gel form to dissolve a solid metal, and not plastic, can be a search item in CLASS 241: "SOLID MATERIAL COMMINITION OR DISINTEGRATION"; and by related subclasses: PROCESSES, /1, "By operations other than force of contact with solid surface"; and /2, "With cell rupturing or liberation of contained liquids"; and as well in /22, "Applications of solid material", and somewhat in /23, ".With heating or cooling of material", and in /24, ".With classification or separation of material", and in /25, "Combined", and lastly in /606, a Cross-Reference Art Collection as "MEDICAL/SURGICAL WASTE COMMUNITION".

Citations in the disinfecting process would be seen in the CLASS 422: "CHEMICAL APPARATUS AND PROCESS DISINFECTING, DEODO-RIZING, PRESERVING, OR STERILIZING", and in these subclasses: CHEMICAL REACTOR, /184, ".For chemically destroying or disintegrating solid waste, other than burning alone", and in a limited degree, /186.01, " . . . Magnetic", and in Classification: "PHYSICAL TYPE APPARATUS" as in /255, " . . . Means separating or dissolving a material constituent". These sub-classes as cited seem the best searches for this patent application.

Several citations can be found in CLASS 423: "CHEMISTRY OF INORGANIC COMPOUNDS", but in two subclasses only at this time: "SILICON OR COMPOUND THEREOF", as in /333, " . . . By precipitating or gelling from silicate solution", and in Silica: /338, " . . . By gelling".

Several citations can also be seen in the CLASS 516: "COLLOID SYSTEMS AND WETTING AGENTS; SUB-COMBINATIONS THEREOF; PROCESSES OF", and in the Subclasses: "CONTINUOUS LIQUID OR SUPER-CRITICAL PHASE: COLLOID SYSTEMS; COMPO-SITIONS AN AGENT FOR MAKING OR STABILIZING COLLOID SYSTEMS; PROCESSES OF PREPARING THE COMPOSITIONS [E.G., MICELLE; THICKENING AGENT; PROTECTIVE COLLOID AGENT; COMPOSITION CONTAINING AN EMULSYING AGENT WITH NO DISPERSANT DISCLOSED; ORGANIC LIQUID EMULSIFIED IN ANHYDROUS HF"; as in /77, ".Aqueous continuous liquid phase and discontinuous phase primarily solid [e.g., water based suspensions, disper-sions, or certain sols, of natural or synthetic ester-wax, beeswax, carnauba wax, or latex dispersion], and as in /81, " . . . The material is substantially pure silica sol", and in /85, " . . . Gel forming step [e.g., peptize"].

Limited citations in searching has been seen in CLASS 502: "CATALYST, OR SOLID SORBENT, OR SUPPORT THEREFOR: PRODUCT OR PROCESS OF MAKING", and in the subclasses: "SOLID SORBENT", /405, ".Inorganic gel containing", and in 406, ".Having intended extraneously added iron group [e.g., Fe, Co, Ni] component", and finally in /407, "Silicon containing". While some of these references seem diverse, they have surfaced during the searching for the containment of the dissolvent in the inorganic silica, or silicon.

Another limited citation is seen in the CLASS: SURGERY, and in the subclass /110, " . . . Having means for preventing reuse of device". This sub-class has appeared in these various patent disclosures as functional in preventing the reuse of hypodermic syringe needles.

In the closing citations in viewing the prior art there seems to be many ways presented that will prevent the medical sharp and syringe needle from being reused. The use of a chemical dissolvent to totally and forever rid the world of a possibly infectious medical sharp, and eliminate forever any reuse of a syringe needle, it seems a worthwhile benefit to society and the medical community to eliminate such undue risks. A syringe needle cannot be reused as there is no needle existing with this novel and unique way of disposal.

There are several related prior art activities with some interaction with medical sharps and syringe needles, such as CLASS 206: "SPECIAL RECEPTACLE OR PACKAGE" wherein selective subclasses would interact in disposal of medical sharps and syringe needles. Another classification is found with CLASS 204: "CHEMISTRY: ELECTRICAL & WAVE ENERGY", and to a lesser degree in CLASS 219: 'ELECTRICAL HEATING" wherein one would find the "fried needle". A final classification would be in the CLASS 516: "COLLOID SYSTEMS & WETTING AGENTS: Subcombinations thereof; Processes of" wherein silica sols and gel forming means are to be found.

BACKGROUND OF THE INVENTION

Of the approximately 350 prior art patents cited herein, and adding the patents in application of approximately 50, and the notice and listing of 77 referenced world patents, there seems a very large number to collate in this Background of the Invention. Accordingly, in as far as it is possible and practicable, these patents have been divided into sections by an arbitrary classification code, and evaluated as to importance by a rating scale, all of which are listed and shown at the beginning of this non-provisional patent in application [see page 1A]. These sections and ratings are so included herewith to aid in clarifying and understanding of the values of these many patents in the prior art.

These prior art patents have been divided into sections of interest and applicable reference as follows:
1. Dissolvent, Solvent, & Etchant that can dissolve stainless steel;
2. Syringe Needles that can be ground up, crushed or bent to be unusable, or destroyed, or encapsulated to be unusable;
3. Smaller Containers for operating rooms, emergency rooms, patient bedsides on a table, or wall mounted, or for a single needle;
4. For other type equipment and sharps, including scapels, stents, catheters, instrument tips, and such;
5. Non-metal and plastic, wood, cotton, fabric & paper;
6. Retracting syringe needles, safety types, and needle covers;
7. Devices to remove or demount syringe needles;
8. Bulk & Large Containers [with wheels] & Waste Systems;
9. Chemical, Electrical, Microwave procedures, and including Steam, Gas, Vapors, or Freezing;
10. Gel & inorganic gellation means.

Additionally, these prior art patents are rated as to their interaction with the content found in this patent in application. These ratings are arbitrary and subjective as to their importance to this patent in application. [see page 1B]
+++ RELEVANT to this patent in application with oftentimes several features and components that are relevant in the cited prior art;
++ RELATED to this patent in application wherein such seems to incorporate rate a feature or component that can be construed as related in prior art;
+ OF INTEREST only, wherein a feature or item can be recognized as similar, but not the same as in this patent in application;
x of no interest in this patent application.

In further understanding of the specific terms of this patent in application, one should consider these terms that are 'part and parcel' of this invention. Definitions herein provided are from 'Webster's New Collegiate Dictionary, 1981 edition, USA]:

DISSOLVENT: from dissolve [Latin and medieval French] 1a. to cause to disperse or disappear: Destroy; 1b. to separate into component parts: Disintegrate; 1c. to bring to an end: Terminate; 2a. to cause to pass into solution [as sugar into water]; 2b. Melt, Liquefy. [then continuing the definition through emotions] [p. 328]

SOLVENT: [from Latin] 1. an unusual liquid substance capable of dissolving or dispersing one or more other substances; 2. something that provides a solvent solution. [p. 1099]

ETCHANT: [from etch, & to include etchant] 1 a. the process of etching; 1 b. the art of producing pictures or designs from an etched metal plate; 2a. an etched design; 2b. an impression from an etched plate. [p. 389]

GEL: [from gelatin] 1. a colloid in a more solid form than a sol; 2. Jelly; vt. as gelled, gelled, gelable, & gelation. Gelation [from Latin] 1. the action or process of freezing; 2. the formation of a gel from a sol. [p. 472]

Of the cited prior art patents, a few are noted as relevant, more as related, and many as 'of note' from the lengthy list referenced at the opening section of this patent in application. It seems that the more cited Class Codes support these prior art patents to be referenced and included within the following section specifically as they appear relevant.

A synopsis of these cited patents follows:

| Cl. Code | +++ | ++ | + |
|---|---|---|---|
| 1. | 4 | 5 | — |
| 2. | 2 | 1 | — |
| 3. | 6 | 13 | — |
| 4. | 1 | — | 4 |
| 5. | — | 1 | 3 |
| 6. | — | 1 | 14 |
| 7. | — | 1 | 6 |
| 8. | — | 3 | 15 |
| 9. | 2 | 13 | — |
| 10. | 3 | 19 | — |
| Totals | 18 | 57 | 42 |

The dominant involvement in this patent in application is the gelling of the compound to be used in cleansing and destroying the medical sharps and syringe needles. The reason for this activity is that the gelling is stabile, long-lasting, and completely efficient, and also, it is inorganic so that it does not deteriorate in decades, or even centuries, while waiting to be used. While under the patents in reference herein, a liquid chemical solution can be used that accomplishes the same task, the liquid can tip over in its container, spill out on surfaces, and it does 'outgas' around where it is sitting to give out an acrid smell and corrode any metal object that is nearby. This formulation for a gel compound does not do any of these things, and so, it is quite safe to store, and to use, and to leave around open as it has no adverse footprint.

In the cited reference classification herein, the gelling compounds are somewhat scattered, and not to be found in this cited area in the medical field. Thus, I will corral the prior art hereby that is somewhat applicable in the dissolvent field, and thereby entraining the ability to dissolve stainless steel hazardous sharps and syringe needles. The activity for silica uses and product development is relatively recent, mostly in the USA from 1920's through the 1950's and 1960's until the use of silicon products have been stabilized, and their development into the marketplace completed that we can see today as caulking, sealing materials, elastomeric compounds, and such. The major developments have involved the sizes of the silica 'sols' and their production issues for the market. In this patent in application the modern developments enable the mixing of our dissolvent acidic component into the silicon compounds that can be formulated for dissolving hazardous sharps and syringe needles quickly and completely. Salient and important developments in silica sols are listed to follow from the prior art as relevant and related to this invention:

| Pat. No. | Date | Inventor | Cl. Code |
|---|---|---|---|
| 1,748,315 | February 1930 | Stoewener | 423/338 |
| 1,751,955 | March 1930 | Stoewener | 423/339 |
| 1,755,496 | April 1930 | Behrman | 423/330.1 |
| 1,798,766 | March 1931 | Stoewener | 502/405 |
| 2,114,123 | April 1938 | Heuser | 423/339 |
| 2,370,200 | February 1945 | Shabaker | 422/129 |
| 2,386,337 | October 1945 | Moyer | 423/335 |
| 2,551,014 | May 1951 | Kimberlin Jr. et al | 502/8 |
| 2,601,235 | June 1952 | Alexander et al | 423/339 |
| 2,731,326 | January 1956 | Alexander et al | 423/338 |
| 2,763,533 | September 1956 | Ashley et al | 423/330.1 |
| 3,047,507 | July 1962 | Winslow | 252/75 |

-continued

| Pat. No. | Date | Inventor | Cl. Code |
|---|---|---|---|
| 3,445,189 | May 1969 | Maat et al | 423/325 |
| 3,782,982 | January 1974 | Pierson | 106/603 |
| 3,967,563 | July 1976 | Wason | 106/288B |
| 4,067,746 | January 1978 | Wason et al | 106/288B |
| 4,244,826 | January 1981 | Swanson | 252/8.55C |
| 4,515,700 | May 1985 | Hitzman | 252/8.55R |
| 4,765,818 | August 1988 | Che et al | 65/18.1 |
| 4,784,982 | November 1988 | Usui et al | 502/410 |
| 4,806,665 | February 1989 | Jones et al | 556/413 |
| 5,236,683 | August 1993 | Nakazawa et al | 423/335 |
| 5,419,888 | May 1995 | McGill et al | 423/338 |
| 5,503,820 | April 1996 | Moffett et al | 423/333 |
| 5,589,150 | December 1996 | Kano et al | 423/338 |
| 5,749,376 | May 1998 | Wilk et al | 128/898 |
| 5,843,743 | December 1998 | Hubbell et al | 435/177 |
| 6,375,914 | April 2002 | Vangbo | 423/338 |
| 6,380,265 | April 2002 | Pryor et al | 516/85 |
| 6,884,822 | April 2005 | Wang et al | 516/111 |
| 7,803,343 | September 2010 | Hua et al | 423/338 |

The next significant classification would be in the use of a dissolvent, a solvent, and an etchant that can dissolve, and destroy, all hazardous metal sharps and syringe needles that are in use today. This would be the class number 1 in the 'Cl.Code' listing wherein such relevant and related art is found. As designated in this invention, dissolving away totally stainless steel in the medical field of endeavor presents scarce and rare citations in the prior art. The introduction of a sharp into the gelled material, even ever so briefly, will blunt away the injecting tip as it is the first to enter into the dissolvent, and then such insertion as it continues into the gel, will sterilize and totally neutralize any infectious residue found on the sharp. Thus, it blunts instantly and then clears off infectious material as it is pushed down into the dissolvent container. 'Clean and Clear' renders the sharp or syringe unusable as such reuse would be equal to pushing a sterile blunt paper clip into ones vein or artery. Its use is over, and it is trash, never to be used again. Here-with follows the cited patents in the prior art:

| Pat. No. | Date | Inventor | Cl. Code |
|---|---|---|---|
| 4,718,447 | January 1988 | Marshall | 137/268 |
| 5,116,415 | May 1992 | Rinehart | 75/711 |
| 5,441,622 | August 1995 | Langford | 204/275 |
| 5,441,623 | August 1995 | Langford | 204/275 |
| 5,749,376 | May 1998 | Wilk et al | 128/898 |
| 6,315,113 | November 2001 | Britton et al | 206/210 |
| 6,637,587 | October 2003 | Britton | 206/210 |
| 8,946,015 | February 2015 | Duong et al | 438/197 |
| 8,974,572 | March 2015 | Uchara | 75/744 |
| 8,979,974 | March 2015 | Nomura et al | 75/364 |

In the following classifications are a listing of ancillary and supporting patents that bear upon the main issues of this invention. In 'Cl.Code' number 2 is found alternative means to dispose of the threat of being stuck by a needle, or an hazardous sharp, by grinding, bending, crushing, destroying, or encapsulating these sharps to render them useless and unusable. However, although these are typical of the prior art in their means, in no case do they deal with contamination, infectious means, out-gassing of vapors, nor do they seek to protect others, as this invention does by just eliminating the hazardous sharp or needle forever, and for all time, by its dissolution into nothing at all. Many of these inventions in this category will require electricity being connected to perform the work, while in the Britton patents cited, only a container to hold the dissolving means, and room temperature without any electricity required.

| Pat. No. | Date | Inventor | Cl. Code |
|---|---|---|---|
| 6,315,113 | November 2001 | Britton et al | 206/210 |
| 6,637,587 | October 2003 | Britton | 206/210 |
| 6,969,374 | November 2005 | Krantz et al | 604/240 |

In this Cl.Code No. 3 are found regular containers suited for table tops, the 'Mayo' stand, treatment counters, nurses stations where a flat surface is stable and available; or an alternative, being affixed to a wall when convenient to be used. In our invention approximately 100 syringe needles are provided space to be placed inside the dissolvent in the container, and alternatively, one-handed placement in individual tubes, or in larger one-handed stable placement for multiple syringe needles, and hazardous sharps.

| Pat. No. | Date | Inventor | Cl. Code |
|---|---|---|---|
| 2,990,113 | June 1961 | Fosbrink et al | 232/7 |
| 4,816,307 | March 1989 | Honeycutt | 428/34.1 |
| 4,936,449 | June 1990 | Conard et al | 206/366 |
| 5,080,251 | January 1992 | Noack | 220/335 |
| 5,271,892 | December 1993 | Hanson et al | 422/25 |
| 5,288,964 | February 1994 | Walker et al | 219/68 |
| 5,413,757 | May 1995 | Kutner et al | 422/21 |
| 5,441,622 | August 1995 | Langford | 204/275 |
| 5,441,623 | August 1995 | Langford | 204/275 |
| 5,482,207 | January 1996 | Nelson et al | 232/43.2 |
| 5,749,376 | May 1998 | Wilk et al | 128/898 |
| 5,947,285 | September 1999 | Gaba et al | 206/366 |
| 6,315,113 | November 2001 | Britton et al | 206/210 |
| 6,637,587 | October 2003 | Britton | 206/210 |
| 6,969,374 | November 2005 | Krantz et al | 604/240 |
| 8,393,488 | March 2013 | Japuntich et al | 220/254.1 |
| 8,397,933 | March 2013 | Finnestad | 220/254.3 |
| 8,505,769 | August 2013 | Finnestad | 220/908 |
| 2005/0072758 | April 2005 | Jackson et al | 219/68 |

In the Cl.Code 4 that lists Other Equipment to include scapels, stents, catheters, and instrument demountable tips, and such to be disposed of. In this invention wherein all such convenient size and accessible devices are to be disposed of, it is this method of dissolving away the possibly contaminated and infectious devices securely and totally in a gelled compound that seems to best way to go. While this is a more extensive field than is shown in the reference material, only one citation of a related means is found in the prior art.

| Pat. No. | Date | Inventor | Cl. Code |
|---|---|---|---|
| 5,441,622 | August 1995 | Langford | 204/275 |

In the Cl.Code 5 wherein the Non-Metal Patents & Plastics would be found in the prior art, again only one significant reference has been found. It would seem that since this invention targets metal, and more specifically stainless steel, as found in the medical appliances that little relevance or significance can be cited in these 'other' type items.

| Pat. No. | Date | Inventor | Cl. Code |
|---|---|---|---|
| 5,120,409 | June 1992 | Hanulik | 204/150R |

In the Cl.Code 6 containing Safety Type Syringes and Retracting Types, there are many patents to be found, but only one patent is noted as related or significant to this patent in application. This disposal means as herein presented will dissolve even the retracted and shielded syringe needles as the chemical compound out gasses up into these removed sites to dissolve away the targeted metal needle. These shielded type syringes do offer an increased measure of safety to anyone in the confrontive types of medical treatment, such as the mobile transport vehicles and in the emergency rooms where the incoming patient is unknown and speedy action is required.

| Pat. No. | Date | Inventor | Cl. Code |
| --- | --- | --- | --- |
| 4,915,698 | April 1990 | Levenson | 604/192 |

In the Cl.Code 7 wherein syringe needles are demounted or removed from its barrel that holds the material to inject, and this removed needle is separated and placed in a secure container for its disposal. In this invention no removal process is required, and no electricity or mechanics is needed to rid the planet of the used syringe needle—it's just gone! Again, only one citation of merit is noted:

| Pat. No. | Date | Inventor | Cl. Code |
| --- | --- | --- | --- |
| 5,482,207 | January 1996 | Nelson et al | 232/43.2 |

In the Cl.Code 8 citing Bulk & Large Containers & Waste Systems that constitutes wheeled containers of many gallons capacity for a bulk transfer of used syringe needles [containers] and hazardous medical sharps, as well as, gauze, bandages, tape, phlebotomy & bloody items, and such to a transfer point for further disposal actions, it can be realized that this invention eases such issues by its simple and straightforward elimination of risk from contamination and infections, as well as, outgassing and vapor transfer of airborne particulates stirred up by movement and transfer activities. This invention in application just simply eliminates all such risk once and for all time.

| Pat. No. | Date | Inventor | Cl. Code |
| --- | --- | --- | --- |
| 5,348,235 | September 1994 | Pappas | 241/41 |
| 5,676,070 | October 1997 | Maganas | 110/245 |
| 2011/0268606 | November 2011 | Glazer et al | 422/22 |

In the Cl.Code 9 wherein Chemical, Electrical, Microwave, inc. Steam & Freezing are contained, there does seem to be many relevant and related patents cited as this classification seems as a 'sweep up' class with many aspects swept up that provide ancillary support to this invention. These various activities do interact with this invention in application as the prior art that concerns safety and disposal of sharps and needles. Since this invention is dominantly chemical in its gelling and dissolving, and entrains inorganic chemistry to perform its 'magic' upon one of the hardest substances that man can make, these ancillary features are often more important in prior art than in this new and novel technique.

| Pat. No. | Date | Inventor | Cl. Code |
| --- | --- | --- | --- |
| 4,816,307 | March 1989 | Honeycutt | 428/34.1 |
| 4,936,449 | June 1990 | Conard et al | 206/366 |
| 5,120,409 | June 1992 | Hanulik | 204/105R |
| 5,271,892 | December 1993 | Hanson et al | 422/25 |
| 5,288,964 | February 1994 | Walker et al | 219/68 |
| 5,348,235 | September 1994 | Pappas | 241/41 |
| 5,413,757 | May 1995 | Kutner et al | 422/21 |
| 5,441,622 | August 1995 | Langford | 204/275 |
| 5,441,623 | August 1995 | Langford | 204/275 |
| 5,482,207 | January 1996 | Nelson et al | 232/43.2 |
| 5,676,070 | October 1997 | Maganas et al | 110/245 |
| 6,884,822 | April 2005 | Wang et al | 516/111 |
| 2011/0268606 | November 2011 | Glazer et al | 422/22 |
| 2005/0287677 | December 2005 | Bossman et al | 436/163 |
| 2005/0072758 | April 2005 | Jackson et al | 219/68 |

The foregoing summarizes the panoply of prior art patents as cited in the opening pages of reference, and these do cover specifically and such ancillary prior art sections that give information helpful in the understanding of this patent in application. There are selective patents with citations from the prior provisional patents [PPA's] that have been noted in the request for benefits as PPA's at the onset of this application. The relevant and related patent art will be described herein to follow.

"In the newer art somewhat relevant to the making of a silicon sol or get would be these two patents of the J. M. Huber Corporation: U.S. Pat. No. 7,803,343 of Sep. 28, 2010 and U.S. Pat. No. 7,553,416 of Jun. 30, 2009 to inventors Hua Duen-Wu, Michael C. Withiam, Francis R. W. Goodwin, and Fitzgerald A. Sinclair, and assigned thereafter to the Huber Corporation of Edison, N.J. entitled: "Caustic Silica Gel Manufacturing and Gels Made Thereby" wherein 'the resultant gel materials exhibit a certain pore size minimum while simultaneously a degree of softness heretofore unavailable. As such, not only is this novel method more efficient in gel manufacture, but the resultant materials are novel as well. The gel materials made therefrom may be utilized in a variety of end uses, such as cooking oil filtration, soft skin cleansers, dental abrasives and the like.' [col. 1, lines 15-22] While these inventors show their novel means that supports the uses of any silica gels to incorporate the various materials, both caustic and acidic, to make up end products such as this dissolvent [acidic] into a stable and useful product. They further state: 'In more detail, hydrous silica gels are the result of the classical reaction of an alkali silicate with a mineral acid. Sulfuric acid is the most commonly used acid, although other mineral acids such as hydrochloric acid, nitric acid or phosphoric acid can be used.' [col. 1, lines 52-56] What these inventors demonstrate is that the silica gel can be formed up, and can incorporate material, such as is involved in this patent application in the final adsorption of an acidic dissolvent.

"In the next two Huber patents, U.S. Pat. No. 7,125,432 issued Oct. 24, 2006 to Yong-Hui Huang of Maryland, and assigned to the Huber Corporation of New Jersey entitled: "Method for Making Precipitated Silica or Silicate Compositions and Products Thereof" wherein the inventor states: "Precipitated silicas and/or silicates find uses in a broad range of manufactured products ranging from cosmetics and food products to industrial coatings [such as paper for one example] and elastomeric materials, such as tires. Silicas are particularly useful in dentifrice products [such as toothpastes] where they function as fillers, abrasives, and thickeners, as well as anti-caking agents and glidants for food and pharmaceutical uses. Because of this functional versatility, and also because silicas have good cleaning ability, are relatively safe, and have high compatibility with typical dentifrice ingredients like humetectants, thickening agents, flavored agents, and therapeutic agent such as anti-caries agents, there is a strong desire among toothpaste and dentifrice formulators to include them in their products. Silicates are utilized as active ingredients, such as oil absorbers and odor absorbers, as some examples, as well as additives for various physical and chemical purposes, such as viscosity modifications, again, as one example within a number of different formulations, such as personal care compositions, antiperspirants, and other like products, and paper coating agents and/or anti-caking agents.' [col. 1, lines 29-49] What has been shown in this patent is the versatility of the silica sans silicates to make up many manufactured products that are useful in today's environment. In this patent application these cited uses show the acceptability of using and manufacturing a silica gel product that can be a metal dissolvent for medical sharps.

"A recent patent cited is the U.S. Pat. No. 7,824,665 issued Nov. 2, 2010 to Koji Miyamoto, Yoshimi Sekine, Hiroki Fukui, and Kenshiro Shuto—all of Tsukuba, Japan—and entitled: "Disinfectant Gel for Hands", and assigned to NOF Corporation of Tokyo, Japan wherein the inventors have a non-sticky, fast drying disinfectant, benzalkonium chloride, that is an improvement over the typical soap with residues and oils and/or 'scum'. They describe their new gel as it contains '0.01 to 2.0 wt % of a maleic anhydride polymer, 0.01 to 5.0 wt % of polysaccharides, 40 to 95 wt % of a lower alcohol, and water, with the total being 100%.' [source: Abstract & col. 1, lines 52-55] It is important to recognize the uses and versatility of gelling material into useful products that today seems commonplace, and a few years and decades previous was not understood well, and it was awkward and difficult. Today both base and acid compounds are placed into a gel product without untoward difficulty, and as in this invention application a gel product can evolve that incorporates acidic compounds that can dissolve the 400 series of stainless steel and as such eliminates any transfer of infectious material as the steel is gone.

"The following two patents assigned to Simax Technologies, Inc., of Irvine, Calif.: U.S. Pat. No. 7,026,362 issued Apr. 11, 2006, and the U.S. Pat. No. 6,884,822 issued Apr. 26, 2005, both identically listing the same inventors, all of California: Shiho Wang, Yasar Halefoglu, Chih-hsing Cheng, Dengfeng Xu, David Kwong, Nung Chan, Mengying Chen, and Chinh Do, and both entitled: "Sol-Gel Process Utilizing Reduced Mixing Temperatures" wherein these patents and others of the Simax patents are directed to glass making and ceramic materials, but in this process, there is shown activities that aid in comprehending this patent application. In their production of a dry silica gel they gain larger particles and increased pore radius by selectively using hydrochloric [HCl] or Hydrofluoric [HF] acid, Oxalic acid, and oftentimes Hydrochloric acid." [col. 2, lines 17-23] Further details are shown on the sizing and gelling and drying of silicas in their Column 4, lines 8-23, wherein the quality and delaying times can be made into gelling so that ordinary and routine additives can be joined in effectively as too short a setting up of a gel can block these desired features. In this invention application such features can be useful in the forming of this dissolvent gel in the proper strength with additives, and their placement into a receptacle for final use by a client.

"In the U.S. Pat. No. 6,500,870 issued Dec. 31, 2002 to Magnus Olaf Linsten, Bozena Stanislawa Tokarz, and Kenneth Olaf Larrson, all of Sweden, and assigned to Akzo Nobel N. V. of Arnhem, Netherlands, entitled: "Method for Manufacturing of Silica Sols" wherein in the 'Summary of the Invention' is one sentence: 'The invention is a method for producing a high purity silica sols using a phosphonic acid-based complexing agent, and the high purity silica sols produced there-from.' [col. 2, lines 2-4] While the inventors intension is shown to create high quality silica sols for 'water polishing' of high grade silicon chips, the details as described in their invention reflect means of making a pure product that this invention application would not require, but could benefit from, in the mixing of its gel product that disintegrates and dissolves the stainless steel and other metals.

"In the U.S. Pat. No. 6,110,439 issued Aug. 29, 2000 to Ravindra Deshpande and Lisa A. Stover, both of York, Pa., and assigned to Armstrong World Industries, Inc., of Lancaster, Pa., entitled: "Dry Silica Gel and Process of Preparation" wherein a typical wet silica gel is cleansed of extraneous metals and 'then dryed to obtain either a xerogel or aerogel product, this dried product is further remarkable in that it has a very fine pore structure.' [col. 1, lines 55-58] What is of interest here is the final dry gel product that can be manufactured as a dissolvent gel product.

"While these various cited patents contain different ways and means in total, they do indicate that it is possible to manufacture a dissolvent gel product as in this invention application that is acidic in its pH level. While the product lines achieved are different, it does show that this invention herein can be produced as indicated in the Ralph Iler book as cited in the prior Reference Section, and that this invention thusly is possible as the next section shows.

"To continue the basis for this invention we consider in this field of art several distinct uses that incorporate technology in vastly different areas from what this invention concerns. Wherein this invention under application utilizes a gel form of a chemical compound to dissolve metal sharps, these other fields of endeavor involve typically automotive batteries, and the sealing up of deep well formations below ground in order to force up more oil to the surface, and other uses to follow. While some uses appear in foods, candies, medicines and such, none are in this chemical dissolvent field of endeavor, and even fewer remain in the inorganic arena wherein this invention is located . . . .

"In the maximizing of oil and gas well production, and in certain situations, the strata of porous rocks, such as limestones, doloemites, and other calcarious materials, will reduce or impede normal production of a drilled well. It is common practice in such situations to "fracture-acidize" these formations in an attempt to increase the oil and gas production. An aqueous acid is typically injected into the well bore to fracture and seal the porous strata to provide a conductive flow up to the earth surface. In the common use of up to 28% hydrochloric acid can be used to stimulate the existing well production; however, the reaction of the acid with the carbonate rock occurs at such a fast rate that the acid is depleted rapidly. Such rapid depletion of the acid results in a very limited depth of penetration and the desired production activity is forestalled. It has been discovered that retarding the rate of the acid depletion can be accomplished by creating an acid gel solution and other similar means such as chemical retarders, foaming of the acid, emulsifying the acid, and cross linking with acid viscosifying agents. An improvement in this technology is seen in U.S. Pat. No. 4,624,795 issued Nov. 25, 1986 to Jeffrey C. Dawson et al, entitled: "Aqueous Acid Gels and Use Thereof", and this patent is the source of some of the information above as extrapolated from its "Background of the Invention", col. 1, lines 6-28. The Dawson patent uses, as stated in its Abstract: "Copolymers of a predominant proportion of an olefinically unsaturated sulfonic acid, an acrylamide, a vinyl phosphonic acid, and optionally other copolymerizable vinyl monomers, form aqueous acid gel compositions when added to the aqueous acid along with a gelling agent selected from titanium or zirconium compounds, and retarded gel destabilizing compounds containing fluoride, sulphate or phosphate anions, the apparent viscosity and time of stability of the acid gel composition being controlled by the addition of these essential ingredients."

"In the U.S. Pat. No. 4,515,700 issued May 7, 1985 to Donald O. Hitzman of Oklahoma and assigned to Phillips Petroleum Company, entitled: "Gelled Acid Composition", one sees a different approach in materials useful in increasing the output of an oil and gas well. This invention is summed up quite well in its Abstract: "A stable polysaccharide gelled acid is produced by heating a polysaccharide solution which has not previously been heated in excess of 60 degrees Fahrenheit at a temperature from about 60 degrees Centigrade up to a boiling point of the polysaccharide solution for about 5 minutes to 120 minutes and subsequently adding acid. Preferably, the polysaccharide solution when heated contains a phenol or aldehyde." The essential difference here being the compound of a polysaccharide as the gelling agent.

"Another approach in the treatment of oil and gas wells is seen in the U.S. Pat. No. 4,317,735 of Mar. 2, 1982, issued to Curtis W. Crowe of Oklahoma and assigned to The Dow Chemical Company, entitled: "Method of Inhibiting Crosslinking of Aqueous Xanthan Gums in the presence of Ferric Acid Ions". Again, the purpose of this invention is well stated in its Abstract: "Aqueous xanthan gums normally crosslink at a pH greater than about 1.5 in the presence of ferric ions. This phenomenon is undesirable under many conditions of use, such as acidizing treatments of wells, and is inhibited or prevented by adding certain soluble alkanoic and/or alkenoic acids to the system. The alkenoic and alkenoic acids have at least 4 carbon atoms and bear at least 2 alcoholic hydroxyl groups per molecule and can be added as the organic acid per se or as a soluble salt or y-lactone. Ascorbic acid and erythorbic acid are examples." In this patent one sees organic compounds providing a variation of the usual gel acid compound in such well treatment, and one can realize the range of available gels that will thicken an acid and a salt.

"In another earlier patent also assigned to Phillips Petroleum Company, U.S. Pat. No. 4,244,826 of Jan. 13, 1981, issued to Billy L. Swanson of Oklahoma, the same concept of polysaccharides and related thickening agents was published. Additional patents on the same concepts are issued to Billy L. Swanson in U.S. Pat. No. 4,205,724 on Jun. 3, 1980, assigned to Phillips, and U.S. Pat. No. 4,103,742 on Aug. 1, 1978, and also assigned to Phillips, shows similar chemical concerns for fracture/sealing of an oil and gas well using gelled acid compounds.

"While the techniques and purposes of gelling acids may be different in these cited patents, many of the compounds and means of putting together the components provide useful knowledge for this invention. Let us continue now to see how this invention deals with a chemical dissolvent for metal sharps and such.

"The most relevant art seems to be the two patents of Richard Britton concerning syringe needles and medical sharps disposal, and I am a co-inventor on the first issued U.S. Pat. No. 6,315,113. However, as both patents do concern a liquid, even up to a viscous liquid, for said dissolving of the metal medical sharps, in this current patent application a gelling is cited that accomplishing a similar dissolution, it is not a liquid. The use of an inorganic gel seems to solve a number of general safety and usage issues that have been presented over the several years of effort to put this new technology to practical use. Of course, the prior art for any acid gelling shows up in patent art for oil wells, batteries, and some in containment of waste products. It does seem timely to discuss such art as it is cited for reference.

"An additional prior art in the medical field is the inclusion of several patents for a single-handed containment of used single-use syringe needles, and such is cited as U.S. Pat. No. 6,659,277 issued Dec. 9, 2003 to Geaorge D. N. Coletti and Walter W. Bond, both of Georgia, USA, and not seen as assigned wherein the intended procedure involves an adhesive block capable of retaining a syringe cap for its removal with 'ease' and the then recapping procedure again using the adhesive block to hold the intended syringe cap after use 'firmly' in place so that an easy and safe recapping can take place. Inventors Coletti and Bond have an additional and similar earlier U.S. patent, issued Feb. 19, 2002 as U.S. Pat. No. 6,348,044 with these identical features. In these cites patents pertaining to medical uses, the classification has all been in the 'Class 206: SPECIAL USE OR PACKAGE' as they have concerned the containment and safety issues for disposing of used hypodermic syringes and other hazardous medical sharps.

"In the field of silicas and their manufacture and uses, several patents can be useful to cite. In the U.S. Pat. No. 5,871,867 issued Feb. 16, 1999 to Ralf Rausch, Heinz Esch, Robert Kuhlmann, Guenter Tierk, Karl Meir, and Walter Meon, all of Germany, entitled: "Precipitated Silica" and assigned to Degussa Aktiengesellschaft of Frankfort, Germany wherein the many stages and means of producing precipitate silica are described, and as such indicative wherein such means show how to ameliorate an acid into inorganic silica. In the U.S. Pat. No. 4,461,892 issued Jul. 24, 1984 to Masahiko Nishikawa, Hiroaki Ishibashi, and Hidenori Furukawa, all of Japam, entitled: "Process for Preparing Porous Spherical Cellulose Particles" and assigned to Chisso Corporation of Osaka, Japan wherein the particles are gelled to become a means for filtering, embodying acid mans or alkali means, for the manufacturing of selected size and shape desired as an end result. Excellent charts and diagrams are shown for such means, even though in an organic framework and process, and as such, not of direct bearing upon this patent application.

"In the added search field endeavor, several waste containment prior art patents seem timely to include herein with U.S. Pat. No. 6,203,484 issued Mar. 20, 2001 to Anthony Lepore of Canton Mich., USA, and Siegfried Lang of Ludwigshafen, Denmark, entitled: "Methods for Disinfecting Wastes", and assigned to BASF Corporation of Mt. Olive, N.J. wherein iodine complexes are gelled to disinfect and stabilize any biohazardous and infectious waste. Certain iodine complexes can also dissolve some metal, and certainly offer strong disinfecting means to any gelling undertaken, and as such, are of natural interest for this patent application, albeit not germane at this time. Another waste control patent of cited reference is U.S. Pat. No. 5,843,743 issued Dec. 1, 1998 to Jeffrey A. Hubbell, Chandrashekhar P. Pathak, Amarpreet S. Sawhney, Neil P. Desai, Jennifer L. Hill, and Syed F. A. Hossainy, entitled: "Gels for Encapsulation of Biological Materials", and assigned to The Board of Regents of The University of Texas System, of Austin, Tex., wherein the gelling means is intended to encapsulate the biological materials safely. Excellent charts and research data can be seen in this patent and its drawings, but even so, the means such as used in this patent application would be more for an ultimate, safe, and convenient means of disposal, and not for any usage as the Hubbell patent undertakes.

"The intended citations of such diverse prior art is more the result of a lack of any direct and applicable art such as in Britton and myself in this field so that these many aspects are to be cited and investigated for their possible interaction and claims. It does seem that the cited prior art not so direct can have a related and relevant material to consider as this invention application evolves to build a safe and satisfactory gel to contain and allow safe disposal of metal scrap and medical sharps." [The prior 18 paragraphs are from the Provisional Patent Applications herein cited as a benefit at the onset of the current patent application]

The means and methods of producing organic, and then into the more difficult inorganic, gelling of silicas has a lengthy history in chemistry, and subsequently being combined with acids as in this invention, has proven itself somewhat difficult as will be reviewed in the next section to follow.

HISTORIOGRAPHY OF THE SILICA GELATION

In the description of the properties and chemical preparation of a "Silica Gel" from the reference sources cited on the title page of this application of "The Handbook of Preparative Inorganic Chemistry" as edited by Georg Brauer, in Part III, Special Compounds, Section 1, of "Adsorbents and Catalysts by R. Wagner of Stuttgart, Germany, pp. 1609-1676, one finds the descriptions of the inorganic silica gel, pp. 1648-1652. Here is introduced the uses of acids as commonplace in the preparation of such gels and the indications that gels are tolerant of chemical solutions involving acidic pH levels.

This silica gel being inorganic and with modern development in its packaging and ease of use and availability will serve as our best embodiment. Experience in the commercial battery manufacture has shown this product to be stable, semi-solid/viscous, tolerant of acid and other chemicals such as the dissolvent solution, long-lasting and retentive of its strength without any real negatives or side-effects, and in short, ideal for this invention.

To follow the early preparation and history of the development of silica gel, one can review the introductory remarks of Herr Professor Wagner: "Silica Gel: To start with, 3.4 liters of sodium silicate-sodium waterglass, d20 1.37—is diluted with one liter of water—mechanical stirring—. Then, 10N HCl is added at the rate of 10 ml/min. until thymol blue shows an acid reaction—pH 2-2.8—. After addition of 400 ml of the acid the mixture becomes viscous and rubberlike. The acid addition is interrupted and the mass is broken up. It is then manually stirred while acid is added in drops. The mixing is continued until a thin suspension is obtained. The remainder of the acid is then added at the original rate until the desired pH is reached. The mixture is then stirred for two additional hours at room temperature, suction-filtered and washed until the wash liquid is no longer acid. The gel is dried at 200 degrees Centigrade for 12 hours, ground to the desired particle size, and finally washed free of Cl—. The product is then dried at 250 degrees C. for 24-48 hours. Yield: 1.5 kg.

"Properties 'are': Dull-white gel granules; hardness approximately that of glass; high specific surface—500 m. 2/g.—. Gels prepared according to the above directions are especially useful for chromographic purposes." And so, this description continues on with general characteristics of silica gel. Source: Brauer, op. cit., pp 1648-1650.

More history and detail on the properties of silica gel is found in our reference source listed on the title page as "The Chemistry of Silica" by Ralph K. Her in Chapter 4: 'Colloidal Silica-Concentrated Sols', wherein he explains:

"The term 'colloidal silica' here refers to stable dispersions or sols of discrete particles of amorphous silica. By arbitrary definition, the term excludes solutions of polysilicic acid in which polymer molecules or particles are so small that they are not stable. Such solutions, which are usually obtained by acidifying sodium silicate solutions or by hydrolyzing silicon esters or halides at ordinary temperatures, have been discussed in Chapter 3 as precursors of colloidal particles.

"Stable concentrated silica sols that do not gel or settle out for at least several years became available in the 1940's, after it was learned to make uniform collodial particles larger than about 5 nm in diameter, stabilized with an optimum amount of base.

"When Vail in 1925 and Treadwell and Wieland in 1930 reviewed the status of colloidal silica, only rarely could a silica containing more than 10% silica be obtained; such sols were not stable toward gelling. In 1933 the art was reviewed by Griessbach, who reported that a 10% sol stabilized with ammonia was made by I. G. Farbenindustries, A. G. In 1941 Bird patented a process for removing the alkali from a dilute solution of sodium silicate by a hydrogen ion-exchange resin, adding back a small amount of alkali to stabilize the silica, and concentrating by heating to boil off the water. It is now evident that under these conditions silica particles were grown to 5-10 nm in diameter. In 1945, White patented a process of washing the salts out of silica made by acidifying a solution of sodium silicate, impregnating it with an alkaline solution, and then heating until most of the gel is peptized to a sol. These processes generally gave sols containing 15-20% silica, at least temporarily stabilized against gelling or settling out. In 1951, Bechtold and Snyder developed the first process for making colloidal silica particles of uniform and controlled size, and Rule further defined the optimum concentrations of alkali required for stabilization while limiting electrolyte impurities.

"The history of development and the state of the art in about 1954 was summarized by Iler. Further refinements by Alexander in controlling the particle size, degree of aggregation, purity, and optimum concentration of stabilizing alkali led to stable sols of particles of only 8 nm in diameter, yet containing more than 30% silica. Stable, translucent, aqueous sols containing up to 50% by weight of SiO2 have been developed by making particles 20-25 nm in diameter and adding an optimum amount of alkali for stabilization and sufficient salt to reduce the viscosity without destroying the stability.

"Sols containing discrete particles as large as 300 nm or more in diameter, which settle out on standing, have been made be autoclaving wet silica gel with a base under super-atmospheric pressure and then breaking the lightly aggregated particles apart in a colloid mill.

"Thus in the past 30 years methods have been developed for making discrete silica particles covering the whole range of colloidal size and stabilizing these as concentrated commercial sols." Source: The Chemistry of Silica, op. cit., Wagner, pp 312-313.

In the best embodiment the activity and utilization of silica compounds in the colloidal suspension seems to be the most efficacious method of application, and as such, a further background in the polymerization of these silica compounds seems to be in order. From the cited source of The Chemistry of Silica in the Chapter 3, "Polymerization of Silica", we can cite from its introduction: "From the time of Graham, who made an intensive study of sols and gels, many attempts have been made to explain the behavior of silicic acid. When freshly made by acidifying a soluble silicate or hydrolyzing the ester, silicic acid is not 'colloidal', since it diffuses easily through parchment or animal membranes and has a molecular weight by freezing point depression corresponding to monomer. Soon the molecular units become larger and pass through membranes only slowly and then not at all. This could be because the monomer or other small primary particles form aggregates, or because the individual particles increase in size and decrease in number.

"Freundlich appeared to recognize these alternatives when he wrote: 'Whether it is rather a matter of polysilicic acids, which give larger 'micellae', being formed from Simple silicic acid, or whether the crystalloid particles originally present already consist of polysilicic acids, but are exceedingly fine 'microns' which continually increase in size—cannot yet be said with certainty.

"In his terminology, a 'micella' is a colloidal particle in which foreign substances—ions, water—are present in its structure, that is, a porous aggregate, whereas the 'ami-0cron' is a discrete 'particle' too small to be seen with the ultramicroscope. He recognized that such small particles in a colloidal solution could 'consist of one very large molecule', in other words, a single unit, not an aggregate.

"Because the most obvious behavior of a silicic acid solution is that it increases in viscosity and finally forms a gel, its polymerization was generally assumed to be an aggregation process of a polymerization by which smaller molecular units linked together into larger ones. The nucleation and growth of discrete particles prior to the stage where aggregation begins have not been recognized by many workers, who held to the idea that Si{OH}4 polymerized into siloxane chains which then were branched and cross-linked as in many organic polymers. Even now attempts are still made to apply the idea of monomer functionality and condensation polymerization theory of organic chemistry to the silica system. In fact, there is no relation or analogy between silicic acid polymerized in an aqueous system and condensation-type organic polymers.

After some important work by Kruyt and Postina in 1925, the division of silicic acid sols that can form gels, was outlined to be in two groups: "The first group has a pH of 4.5 or less, and the viscosity of the sol increase with time. On the other hand, pure silica sols, having a pH of 7 or higher, are relatively stable, the viscosity either remaining the same or decreasing with time. This difference in behavior is explained as follows: the more alkaline sols bear a negative charge and are thereby stabilized. However, the addition of soluble salts lowers the charge of the particles and causes gelation or flocculation. On the acid side, where there is essentially no charge, aggregation or flocculation occurs, causing an increase in viscosity, and eventually gelation. Tourky also discussed the structural differences between silicic acids in acidic and basic solutions, firillar or network structures arise through the formation of oxygen bridges between silicic acid units.

"It was Carmen who first clearly stated that silicic acid polymerizes to discrete particles which then aggregate into chains and networks.

"The formation of silica gels can be regarded as taking place in two stages. In the first, initially formed Si{OH}4 condenses to form colloidal particles. In dilute solution, a further slow increase in particle is the only subsequent change., but at a concentration of about 1 percent silica, these primary particles are able to condense together to give a very open but continuous structure, extending throughout the medium, thus bestowing a certain degree of rigidity upon it. In both stages of polymerization, the mechanism is the same, that is, condensation to form 'Si—O—Si' links, but in the first stage, condensation leads to particles of massive silica, while in the second, since it is not possible to fit two particles accurately together over a common face, the number of 'Si—O—Si' linkages between particles is fewer than those within the particles themselves. They are merely sufficient to bind adjacent particles together, in a fixed position relative to one another, and thereby to a rigid, highly porous, tangled network of branching chains . . . .

"Thus three stages are actually recognized:
1. Polymerization of monomer to form particles;
2. Growth of particles;
3. Liking of particles together into branched chains, then networks, finally extending throughout the liquid medium, thickening it to a gel"

Source: The Chemistry of Silica, op. cit., pp. 172-73

It seems important to note that activities that do increase polymerization in silicas, do produce viscous sols, or solutions, and do not form up gels from the increased viscosity. Ralph Iler further substantiates this work by citing again Carmen's experimental data that supports this gel formulation. "There is agreement that polymerization, that is, the reactions that result in an increase in molecular weight of the silica, involves the condensation of silanol groups:

"The term 'polymerization' is used in its broadest sense, the mutual condensation of 'Si{OH}' to give molecularly coherent units of increasing size, whether these are spherical particles of increasing diameter or aggregates of increasing number of constituent particles. Formation and growth of spherical particles is one kind of polymerization that takes place under certain conditions. Aggregation of particles to form viscous sols and gels is another kind of polymerization occurring under other conditions. Both types of polymerization may occur at once." Source: The Chemistry of Sols, op. cit., pp. 173-4, and see FIG. 1.

In one step toward the gelling process of silicas that are in the pH measurement between 2.0 and pH 5.0 to 6.0 that is acidic to neutral, the relative gel time is optimal around the neutral points of pH 5.0 to 7.0. The lower pH solutions tend to gel satisfactorily and stablily, and especially when a salt is added. The dissolvent used in this embodiment is water, acid, and a salt which matches the best gelling activities as the pH tends to be c. 3.5 to 5.0. In FIG. 2 to follow, the gel times of silica sols are shown both in the absence of sodium salts, and with sodium salts.

"At low pH the silica particles bear very little ionic charge and thus can collide and aggregate into chains and then gel networks. If the concentration of 'SiO2' is more than 1% such aggregation may begin as soon as the first small particles are formed. However, at lower concentrations and at pH around 2, the monomer is converted largely to discrete particles before they begin to aggregate. On the other hand, at pH 5-6, a monomer is converted rapidly to particles which simultaneously aggregate and gel so that it is not possible to separate the two processes. The rate of aggregation increases rapidly with concentration so that in any case above 1% silica, aggregation probably involves not only particles but also oligomers.

"The process of aggregation and gelling in the silica system is unique because unlike other metals oxides, the solid phase remains amorphous and appreciably soluble in water and is generally in solubility equilibrium with the monomer. It is essential to understand that while sol is being converted to gel, the growing aggregates contain the same concentration of silica and water as in the surrounding sol regions. These aggregates or 'gel phase' cannot be seen because the density and refractive index of the gel phase are the same as the remaining sol. Thus before the sol solidifies only a slow increase in viscosity can be noted, with little change in other properties, up to a point where the viscosity begins to increase rapidly and solidification occurs at the 'gel point' is to observe when the menicus of a sol in a container no longer remains horizontal when the container is tilted." Source: The Chemistry of Silica, op. cit., p. 176.

"Gelling occurs when about half of the silica has entered the gel phase, which can be thought of as spherical solidified regions in suspension which cause a rapid increase in viscosity when the 'volume fraction' reaches about 0.5.

"After the gel network has been formed, the structure becomes stronger as the necks between particles become thicker owing to solution and deposition of silica." [source: The Chemistry of Silica, op cit., p 176]

In the prior tests to gel this inorganic silica with its components, it seems that 2 cc. of strong HCl acid with 4 cc. of strong HNO3 acid, and a 0.5 g. of FCl as a catalyst, and 6 cc. of colloidal silica will gel into a dissolving compound that will obliterate a syringe needle in about 8 minutes. In this combination, the dissolving time will be faster with more, or stronger, acids; and slower with less quality of the acids [more common in industrial applications], and that the catalyst is useful to balance the ratio for a salt to keep the dissolvent action primed and ready for action.

It can be noted that the inorganic composition of a silica gel has proven very long lasting and durable, which is a great benefit and feature in this new and novel invention. It can observed that one common current usage is in 'caulk' for use scaling cracks and air leakage such as around window frames, and the usual time projected for this product is 20 years durability. The inorganic gelling seems superior as it provides its protection and service over decades, not just months or years. Now, that the background of inorganic gelling has been detailed sufficiently to show how it does work, it will then be time to see how it works for this invention in the following section, 'Summary of the Invention' and with the drawings detailed and described herein in this patent application

SUMMARY OF THE INVENTION

Today's means of disposing of used syringe needles and hazardous medical sharps is just to contain them and haul them somewhere else to be disposed of 'out of sight, out of mind'. In some scenarios grinding them up, bending askew, demounting at the hub, chopping off, encapsulating or securing in plastic or resin, all in all, complexity, motors, mechanics, electricity, and such are required to perform these tasks. Or, conversely, just leave them alone in a box wherein they can remain infectious and active so as to out-gas infectious vapors around the room for someone to breathe. It often seems you go in to work healthy, and you go home infected and sick. Perhaps, when these needles and sharps are finally removed, you can get a 'quick stick or cut' that carries the infection to a new 'home'—you!

In this invention there is a disinfectant gel comprising chemical means to destroy all physical organic material contained in a disposal receptacle. This means of total removal of organic material that can contain diseases, infectious microbes and pathogens, difficult viruses, rotting smelly and gaseous residues, unpleasant odors, organic wastes and such, is achieved by the use of a chemical dissolvent gel which can neutralize all such matter in a disposal container.

This disinfecting gel comprises chemical dissolvent means as a gelled means that contains inorganic silicas that accept water, acids, and a salt. This chemical means is a disinfecting compound through its dissolving means to totally destroy and render sterile, all pathogens, microbes, viruses, diseases, organic residues, and infectious waste material in a disposal container. This disinfectant gel further comprises the chemical means to comprise dissolvent means to dissolve steels, including the difficult stainless steel, of the iron group. The chemical dissolvent gelled means further comprises that the gelled means comprise inorganic silicas that accept water, acids, and a salt in order that the dissolvent means can dissolve metal medical hazardous sharps, including hypodermic syringe needles, and other surgical tools and instruments as requisite. Thus, the chemical dissolvent gelled means can dissolve these hazardous metal medical sharps, singly, and in combinations, but not limited to, these following devices:

a. syringe needles;
b. surgical blades;
c. metal demountable tips;
d. surgical instrument tips;
e. surgical sutures;
f. surgical stents;
g. phlebotomy devices;
h. metal surgical catheters; &
i. disposable metal medical devices.

This chemical dissolvent gelled means further comprises disinfecting means from the dissolvent chemicals to sterilize hazardous medical sharps upon contact with the chemical gel. This chemical dissolvent gelled means further comprises that the dissolvent means will blunt and corrode the hazardous medical metal sharps upon contact with the chemical gel. The outside surface of all such metal sharps, needles, tools, tips, and instruments placed even just briefly into the gel will be blunted so as to be unusable, and they would only perform like having a straightened paper clip shoved into your artery or skin. Also, these devices upon the briefest of entry into a gel compound would corrode the surface into a blackened color, and would have upon the surface a very virulent and distasteful acid surface that would also be very painful to the skin. Thus, the medical devices to be disposed of would never realistically be used again, and as such, they pass away wherever they go—on land or at sea—forever destroyed and forever a waste product. Thus, a disposal means of medical metal sharps and needles by the means of a chemical dissolvent gel would be achieved. This disposal means further comprises that the chemical dissolvent gel comprise receptacles, surgical kits, containers, and other containment means for dissolving the medical metal sharps and needles. Also, this disposal means further comprises safe and sterile dissolvent means for all used medical metal sharps and needles residue after dissolving the metals as possible from the residue. This disposal means further comprises a safe disposal once the residue has been dissolved of hazardous metal sharps and made sterile by disinfectant means for disposal as ordinary waste and trash.

Over many years in our local teaching hospital, tons of medical refuse was incinerated each day wherein a lot of intense heat was manufactured by the usual environmentally unfriendly means, and the 'clean' export was from a flue that carried the 'clean' medical waste downwind to a neighboring county, wherein—not unusual to find a new compound, cross-linked from the medical waste—settling down to the ground on unsuspecting citizens living many miles away. This popular means of disposal was finally recognized and closed—and, possibly, you might to be curious as to how the medical waste was dealt with? You just ship further away to somewhere else for 'land-filling', or export overseas. Problem solved, so we can just pass the problem away to the future, or overseas, or just into the sea.

In the invention detailed herein, no electricity is needed, no motors, no mechanical apparatus, no incineration, no heat is needed to clean up sharps. This invention 'operates' at room temperature [ambient/air temperature], and it is in a gelled form that doesn't spill, or smell, or degrade over many years—even decades—and it goes from golden hue to black when working and finished. But, even when it is black in one spot having dissolved a sharp or needle, it will still work in the same spot, it will just be slower to eat away the metal. When complete and finished up and black everywhere, you just cap it—put the lid back on—and you can throw in the regular trash as it is harmless.

Remember that a 'stick or cut' can give you an infection, and that you can't just give it back! It is now your's forever! Sometimes you don't even need a stick or cut, remember 'Legionaire's Disease' that was pervasive in just one hotel in Philadelphia, Pa., and it was said to be 'contained', and not a problem for anyone. It did surface in Australia not long after, and I hope it rode 'First Class' over there as it is a long way to go. In this invention the sharp or needle is 'clean and clear' instantly, as nothing lives in the acid gel compound, NOTHING! The gel will blunt the sharp or needle tip instantly, and then proceed to dissolve away the remainder until gone completely. And, if remaining in the gel for a while, the interior of the syringe barrel will also be cleaned, free of infection. It has been said that most of the spread of AIDS in remote areas, such as Africa and Asia, has come from the reuse of infected needles. This invention will wipe off the face of the globe, every sharp or needle put into it.

Fifteen thousand particulates per cubic foot, many, many tiny ones, with some medium sized and some large sized particulates, all that can transport disease, virus and infection when opportune and available. This was the information available from a laser counter on the doctor's desk in the teaching hospital. When the cleaning crew came at night after hours, the count spiked to 85,000 particulates per cubic foot when the vacuum cleaners were run as the laser counter collected data. In fact, such a count was mostly benign in an office environment, so what level was recorded in the more active sites, or virulent treatment areas? The most active/highest count area proved to be in the staff and public cafeteria with readings of over 250,000 particulates per cubic foot. So, you butter your roll and place on its plate while you talk to someone for a minute or two, and when you eat it you will have some new friends. Throughout the hospital these new 'friends' are everywhere, and a number of infectious particulates will likely come from the sharps and needles discarded in the containment boxes awaiting pick up for disposal. It's called out-gassing when air circulates around in the emergency and operating rooms, clinic and treatment sites, and even nurses stations and patient areas. You realize that if you get 'Hep C or Hep B' you cannot just give it back. There are many possibilities, and if you work in the hospital and feel 'sick' over time, you quit to stay home, and after unemployment runs out, you can't pay bills and rent, how long is it until you are no longer able to survive, and then you die! So, who says that out-gassing can't hurt you? The hospital administrator, the doctors, the staff—they're very sorry that you don't feel good and can't work anymore.

When you're gone from work for such a long time, you are missed, but the tendency is to forget someone, and disregard why they left work. If someone is not thought about over time, and they are sick, then perhaps, their death was natural and expected. Is a practicing nurse too old to work at 45? If this person was at home and ill for 5 or 6 years, then an early death might be explained and accepted. The use of such an invention such as this one, could possibly interrupt difficult and deadly situations from improper care of the used medical sharps and syringe needles.

The reason for gelling this acid dissolvent is that a liquid can spill, splash, out-gas, smell, turn over, and it can cause trouble that a gelled product will not. There can be a place for liquid dissolvent when used for difficult medical devices, but by trained professional handlers in a separated disposal environment in that after dissolving the residue as waste, it becomes safe and uncontaminated and can then be placed in a normal landfill enclosure. This invention is even better when 'land filled', as it is safe and clean forever, it's just waste junk. Nobody can get hurt, ever, unless they poke themselves by accident. The waste junk is clear and clean of any infectious material as it is just 'plain gone' forever.

BRIEF DESCRIPTION OF THE DRAWINGS

FIG. 6 is a chart detailing proper disposal and/or disinfecting means for medical sharps, needles, and devices.

AN INDEX FOR THE CITED NUMBERS IN THE DRAWINGS

Figure 1:
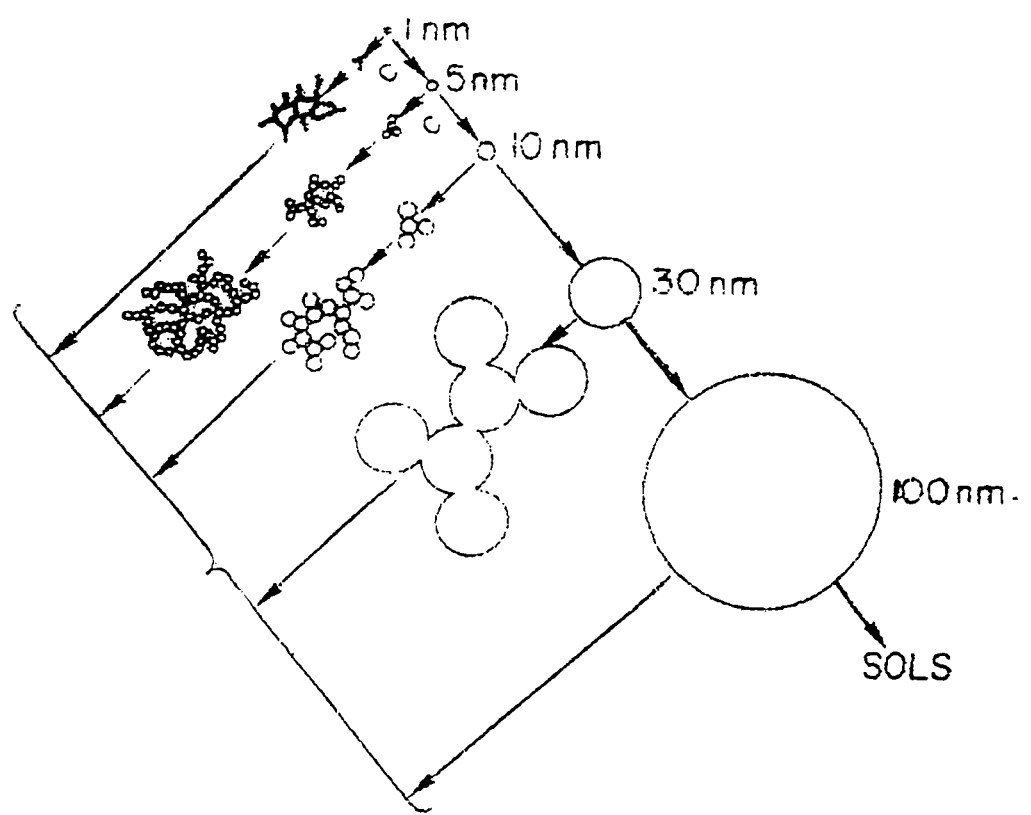
FIG. 1 is a diagram that shows 'the polymerization behavior of silica' and that it will form gels as it grows larger.

| No. | Cited features |
| --- | --- |
| 1 | Dissolvent Gel means |
| 2 | Container, Receptacle, Box |
| 3 | Surgical Kit or Container |
| 4 | Location for Instrument |
| 5 | Surgical Instrument |
| 6 | Lid or Cover |
| 7 | Filter Material |
| 8 | Dissolvent in a Bag or Sack |
| 9 | Grippers: Plastic |
| 10 | Used Syringe Entry Section |
| 11 | Encased Permanent Magnets |
| 12 | Used Syringe |
| 13 | Closing Lid at Entry Point |
| 14 | Safe One-Handed receptacle |
| 15 | -Blank- |
| 16 | Sealing Cover for Plastic Sack |
| 17 | Opening Tab for Cover |
| 18 | Securing Adhesive Pad |
| 19 | Elastomeric Seal for Vapor |
| 20 | Guides for Used Syringes |

DETAILED DESCRIPTION OF THE DRAWINGS

In the drawings that portray the many and varied aspects of this invention in application for a letters patent, there are included chemical diagrams, charts and lists of medical items and their applications, the uses of hypodermic syringes, storage containers for the gel, surgical kits, as well as, the increase of seniors and their facilities, and finally a chart of 'Red Label' Bio-Hazard Waste into 'Green Label' safe waste. All of these many and varied items seem needed to outline more fully the many different possible ways to employ the disinfecting dissolving gel as outlined herein.

In the FIG. 1 there is a diagrammatic chart of the forming of inorganic silica sols that for many decades had proven a difficult task. As has been mentioned herein the inorganic values give this chemical formulation a long-lasting stabile and useful life awaiting its task of dissolving iron group metals, and keeping the gelled basis sterile and without infection or contamination. What is unusual about the uses of silica is that it is somewhat just 'sand' as a silicate of minerals that being hard and inorganic material is very long lasting, certainly the same for many centuries. Herein in the diagram shown in FIG. 1 is that when allowed or forced to grow larger molecules, the silica forms up larger porous, absorbing molecules that are hydrophilic to gather up water, or liquids, such as acids and salts. Silica is also unusual in that it provides a basis for computers to be built, which is what this document is being prepared on. Let us continue to review the next several figures, as they further the knowledge of silica.

Figure 2:
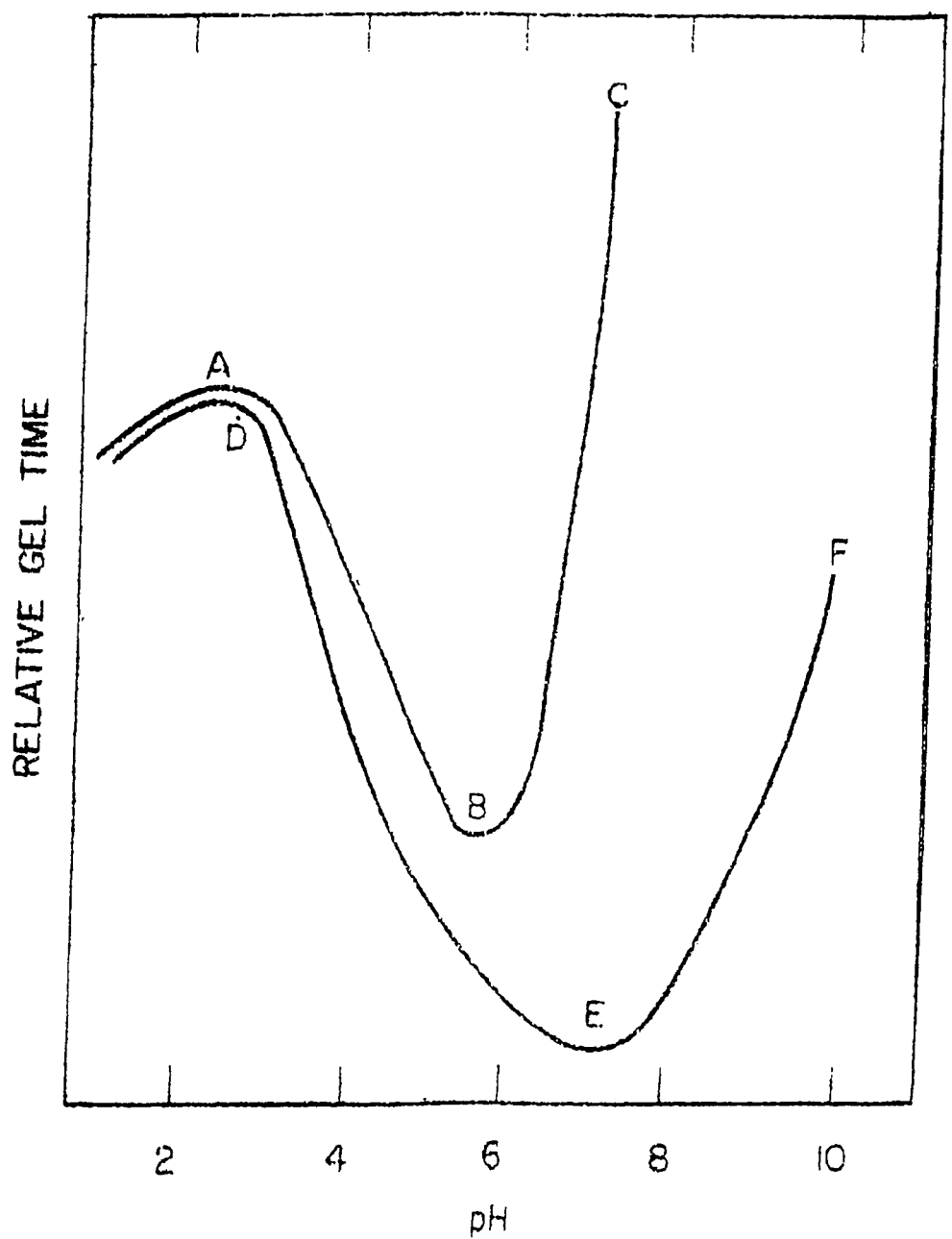
FIG. 2 is a diagram that shows 'the effect of pH on the gelling of silica sols' wherein optimal times are provided with sodium salts.

In the FIG. 2 there is seen a diagram of the optimal mixture and relative amount of time needed to create the required gels. The gelling time seems the quickest at #B and #E which does operate optimally at the pH of about 6 which is about neutral, neither acid nor salt [base]. It seems that this presents a workable model to form up gels, and especially so as the gels herein do contain both acid and salt to dissolve the very strong and durable stainless steel of the 400 series found in the metal medical devices. Too much acid will slow down the amount of time needed, as will, too much base, and so, it needs to just right in its formulation. 'Just right' will allow the gel to be set in its container without undue disruption of the desired formulation. It soon becomes evident that this invention achieves unique features by incorporating the disinfecting means with the dissolving means to totally wipe out the iron group metals in the medical devices. Such a magic sweep is performed by a carefully formulated measure and variation of 'the Royal Acid' as the only known compound being able to dissolve gold. Even Andrew Carnegie published that the dissolving of steel was known, but not to be broadcast out to the public for obvious reasons, and the Royal Acid was published in history by the Ottoman Empire in the 13$^{th}$ century, and likely based upon much earlier information from Romans and Greeks. What is unique herein is the use of gelling an acid and a base by inorganic means.

Figure 3:
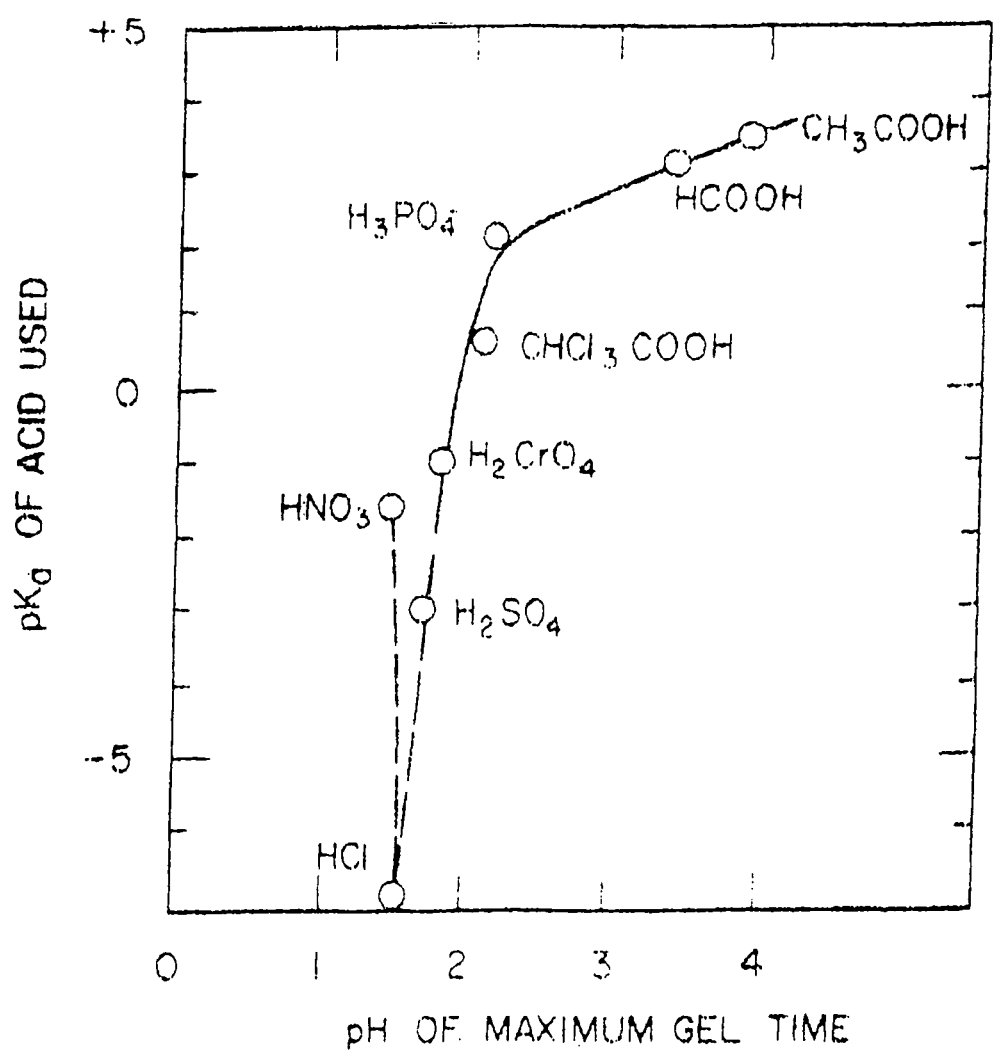
FIG. 3 is a diagram that shows the gelling time and the type and strength of acids proven best.

In the FIG. 3 there is another type of diagram presented wherein for this invention there is a dotted line that is straight up from the HCl [Hydrochloric Acid] to the HNO3 [Nitric Acid] at the left side of the diagram. This seems ideal for this invention as these are the two acids that are most common in use, and the ones targeted for dissolving herein. Needless to say, albeit quick and complete as these two acids are in forming up the disinfectant and dissolvent gel, it is also another benefit in that they are extremely competent disinfectants wherein all organic material can be neutralized quickly and totally with these two acids. While there is presented evidence of many acids that can be used, the selection and ratio of strength seems optimal in what is used for this invention in application. A careful and considered formulation will lead to the very best in disinfecting and dissolving the 400 series stainless steel medical devices forever, so as to never be a hazard or danger to anyone, as they will be dissolved away forever.

Figure 4:
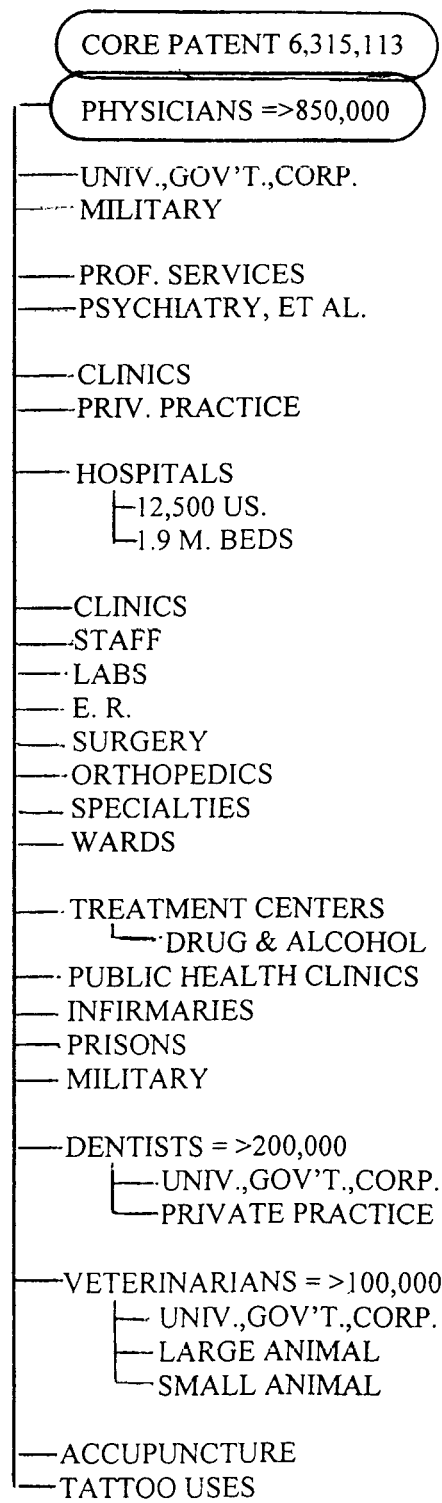
FIG. 4 is a chart from existing patent of Britton and Woodward wherein the many types of medical facilities are listed that can benefit from this gel dissolvent.

In the FIG. 4 there is a drop down chart based from the core liquid dissolvent U.S. Pat. No. 6,315,113 created by Richard B. Britton and Malcolm P. Woodward issued Nov. 11, 2001 that lists the many places that such safe and total removal of potential risks can be effective. The reason such a chart is useful is that it indicates many possible places that a disinfectant and dissolvent gel can be of use. While an indication of the number of active practicing physicians is included, there more when the semi-retired doctors, and the academic and research and laboratory doctors and the supporting staff are factored in, as well as the many doctors in government and military service are added, and to include the many medical practitioners, nurses, emergency and rescue staff, and others associated within the hospitals and clinic. Additional involved people would include the eldercare, rehab facilities, jails and police, and other related activities, all of which can total up to a rather large number of involved people.

Figure 5:
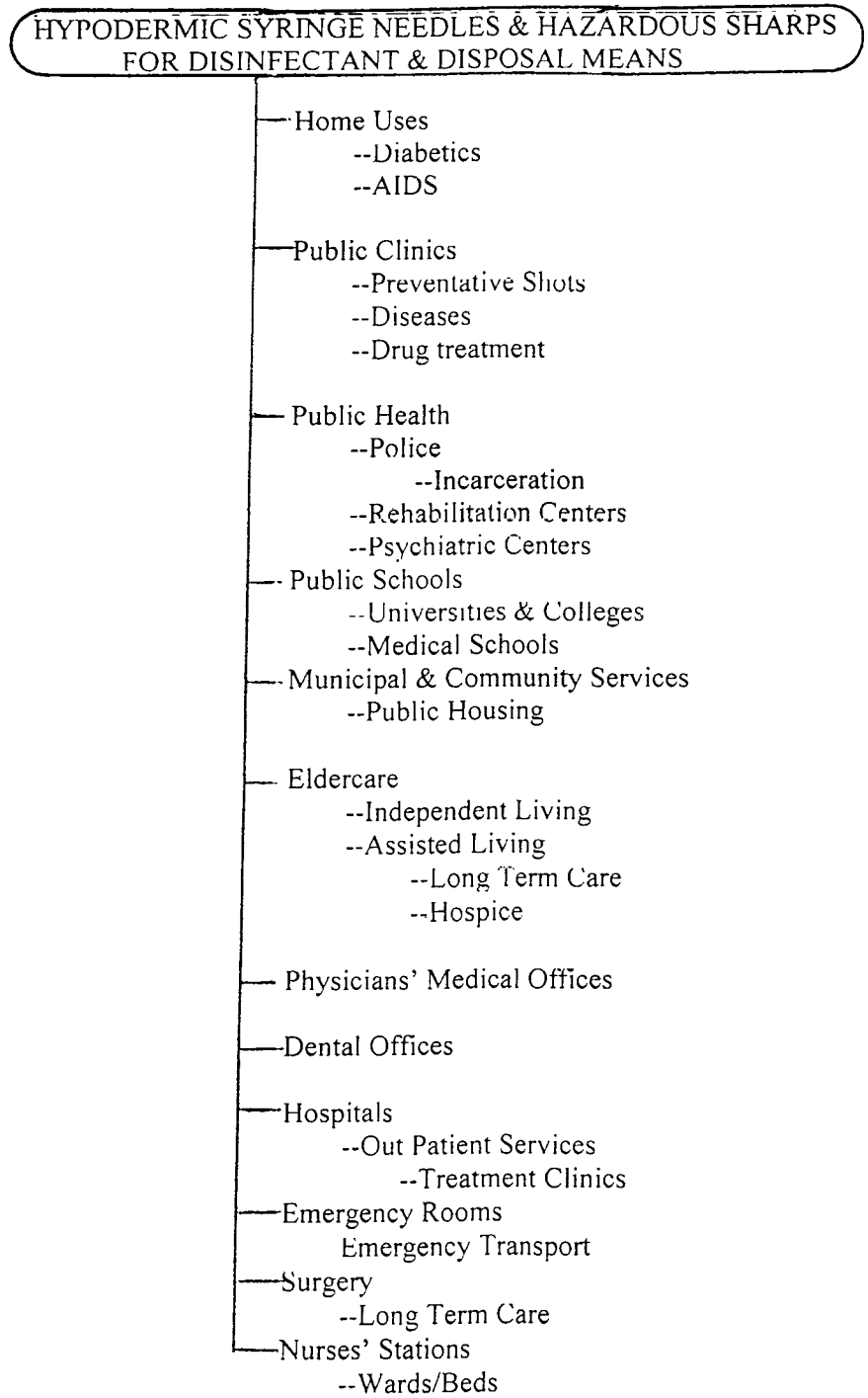
FIG. 5 is a chart detailing locations requiring safe disposal means for medical sharps and syringe needles.

In the FIG. 5 there are listings of similar involved people and adding to the total number would be dentists, and as well, home use, and public concerns such as public clinics, public health, public schools, and the municipal and community services, and to expand eventually to office and commercial buildings, industrial facilities, private schools and universities, and somewhat into stores and small offices, and into the travel and transport industry. A safe and total removal of the hazardous of medical metal sharps and needles would serve every interest across the nation and the world.

The FIG. 6 that follows shows a listing of the different ways that disinfecting and dissolving can apply to selected medical devices, and projects that certain expensive surgical and medical devices can be reused after they are sterilized carefully and completely.

Figure 7:
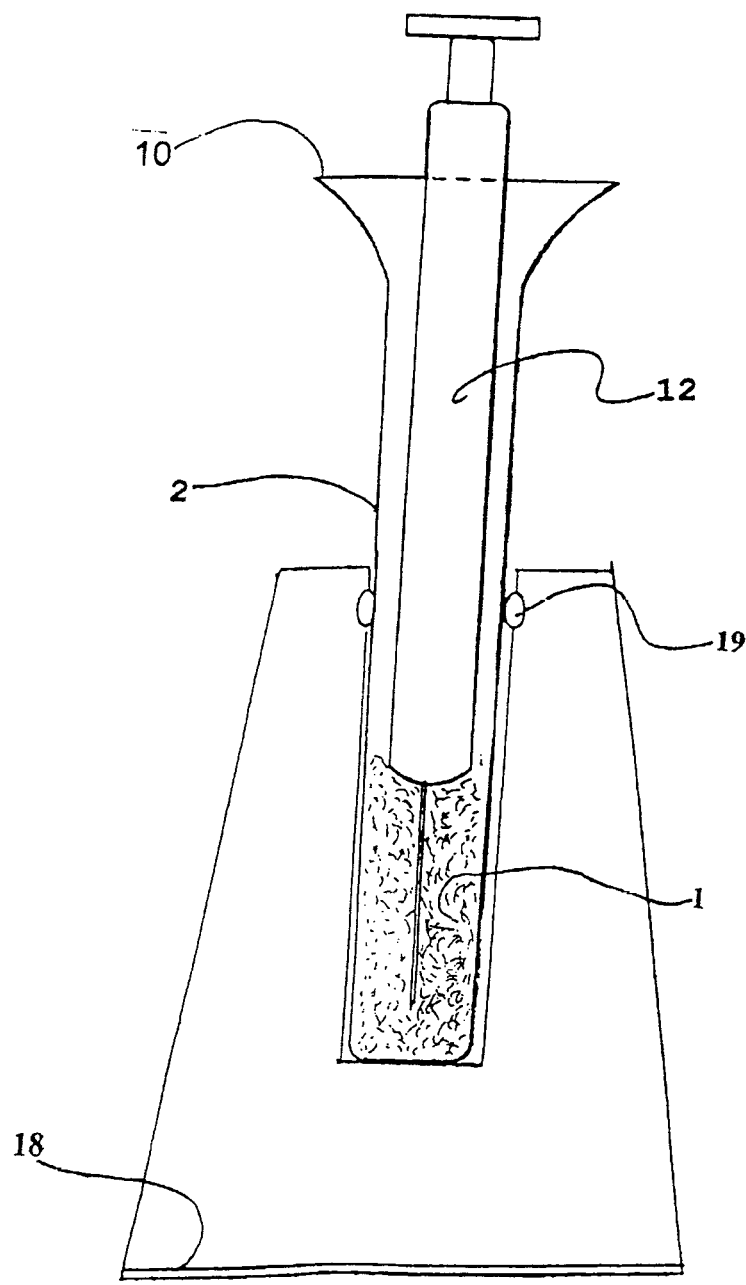
FIG. 7 is a side view showing a used hypodermic syringe having been placed in a wide-mouthed test tube type container situated in a stabilized holder wherein the needle is in a dissolvent gel compound for its final disposal.

In the FIG. 7 is shown a single hypodermic syringe [12] that is to be disposed of, possibly after use in an unsafe environment, and the syringe [12] is located in a test-tube type disposal holder [2] with a wide mouth for easy insertion [10] of the syringe, and also having elastomeric grippers [19] to aid in keeping the tube [2] in its place in a disinfectant and dissolvent gel [1]. This entire holder [2] is shown placed in an adhesively mounted [18] table top main holder that assures the safe removal of the syringe needle [12].

Figure 8:
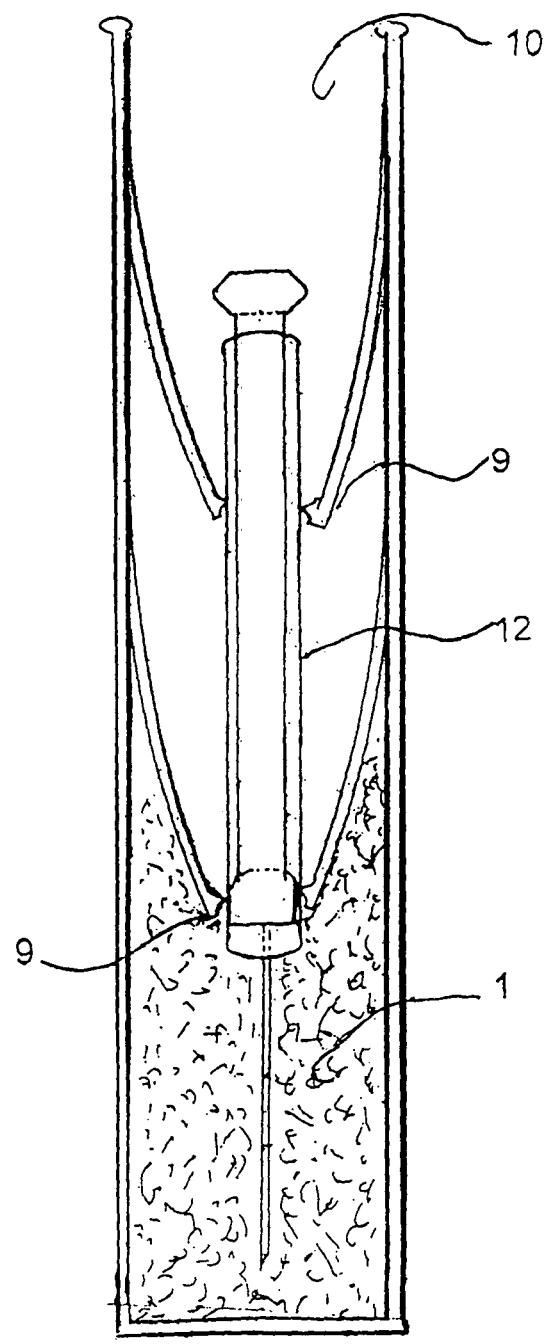
FIG. 8 shows a side view section of a used hypodermic syringe having been placed in a test tube type holder with 2 sets of grippers shown that stabilize and center the syringe in a dissolvent get for its final disposal.

In the FIG. 8 is shown another test tube type holder as seen in FIG. 7 with a wide mouth entry [10] for a used syringe [12] to be placed into a disinfectant and dissolvent gel [1] wherein it is secured in place through the plastic arms/grippers [9] to remain centered in the gel compound [1].

Figure 9:
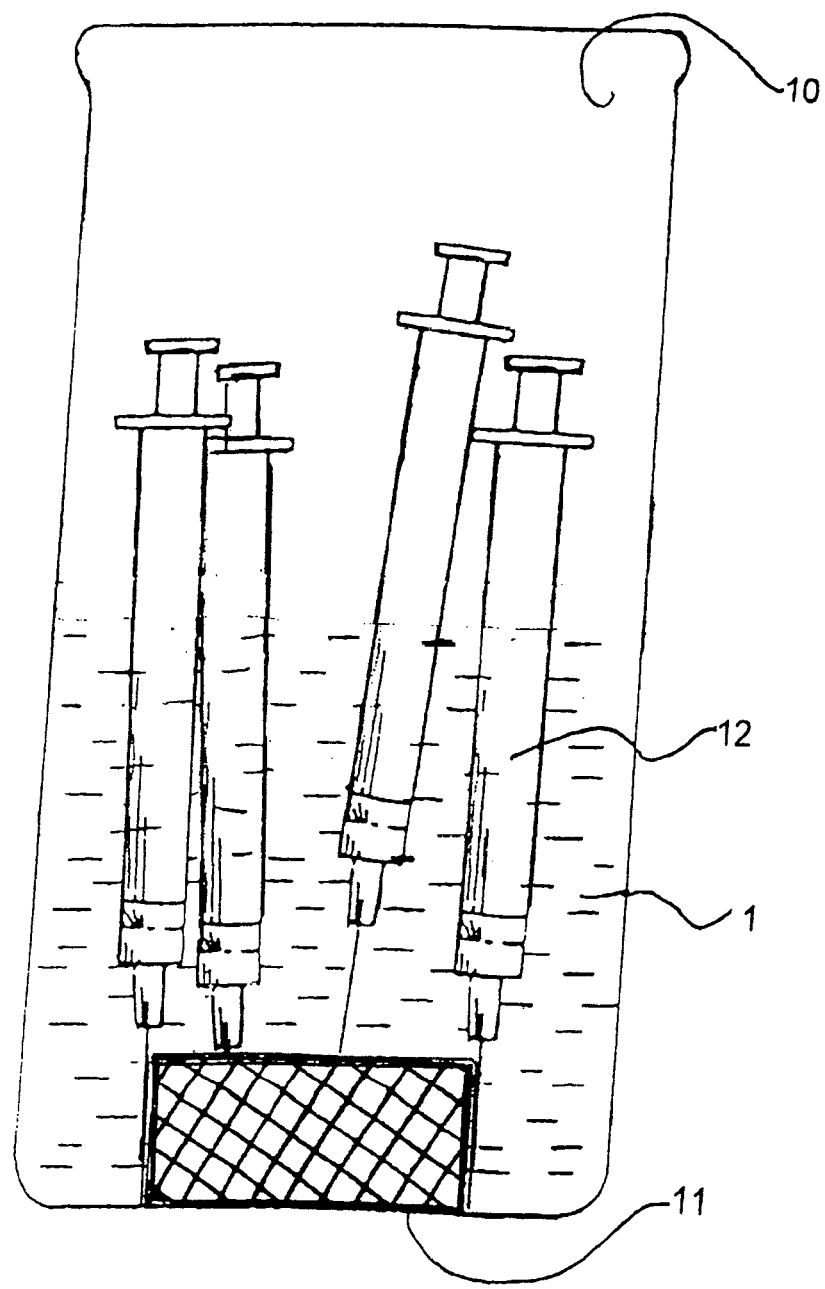
FIG. 9 shows an open container wherein used hypodermic syringe needles having been drawn point down against an encased permanent magnet for final disposal in the dissolvent gel.

With multiple hypodermic syringes [12] in the container shown in FIG. 9 they are drawn down to an encased permanent magnet [11] located on the bottom of the container. The wide mouth opening [10] at the top of this container that would have a fitted lid available [not shown] to seal it off when its task is completed in the disinfecting and dissolving gel [1] therein.

Figure 10:
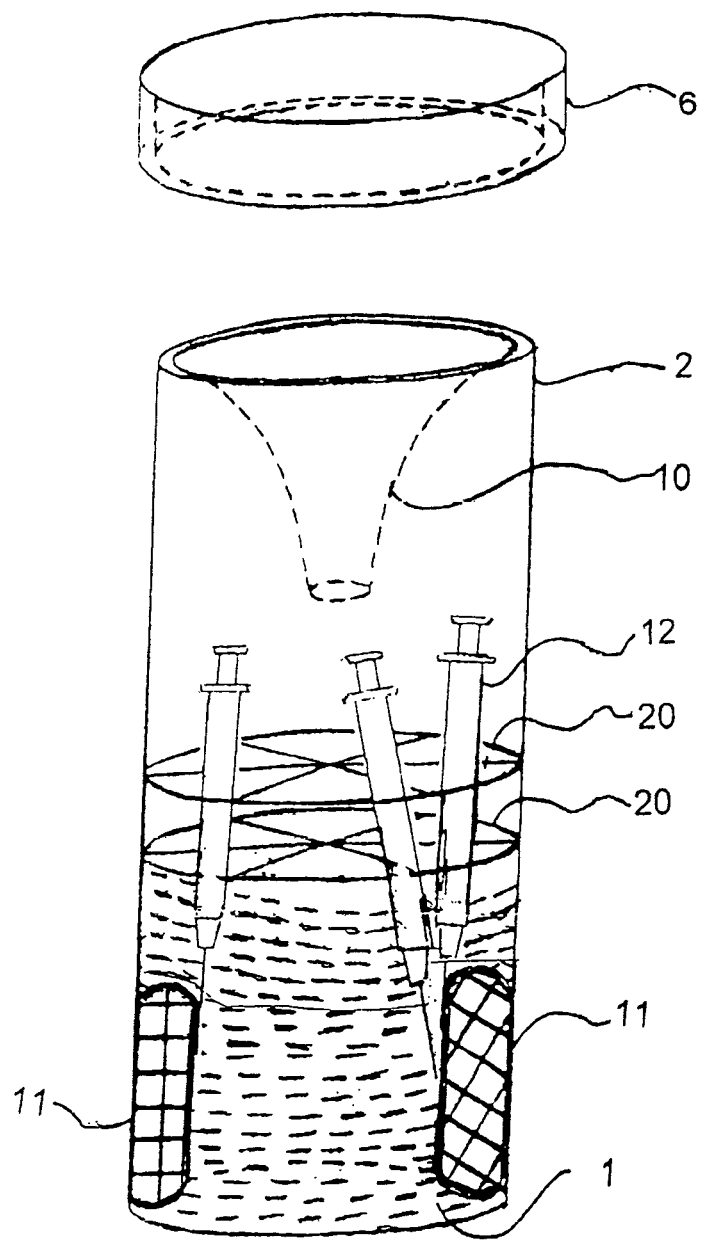
FIG. 10 shows another type of container and its lid wherein the used syringes are drawn downward into the dissolvent gel through guides for their final disposal.

In the FIG. 10 there is a more complete representation of a container [2] with its lid shown [6]. The entry point shows a funnel means [10] just as a wide mouth would be, to direct the used syringes [12] through interior guides [20] into the disinfectant and dissolvent compound [1] at the bottom wherein two encased permanent magnets [11] draw down the syringe steel needles for their ultimate destruction.

Figure 11:
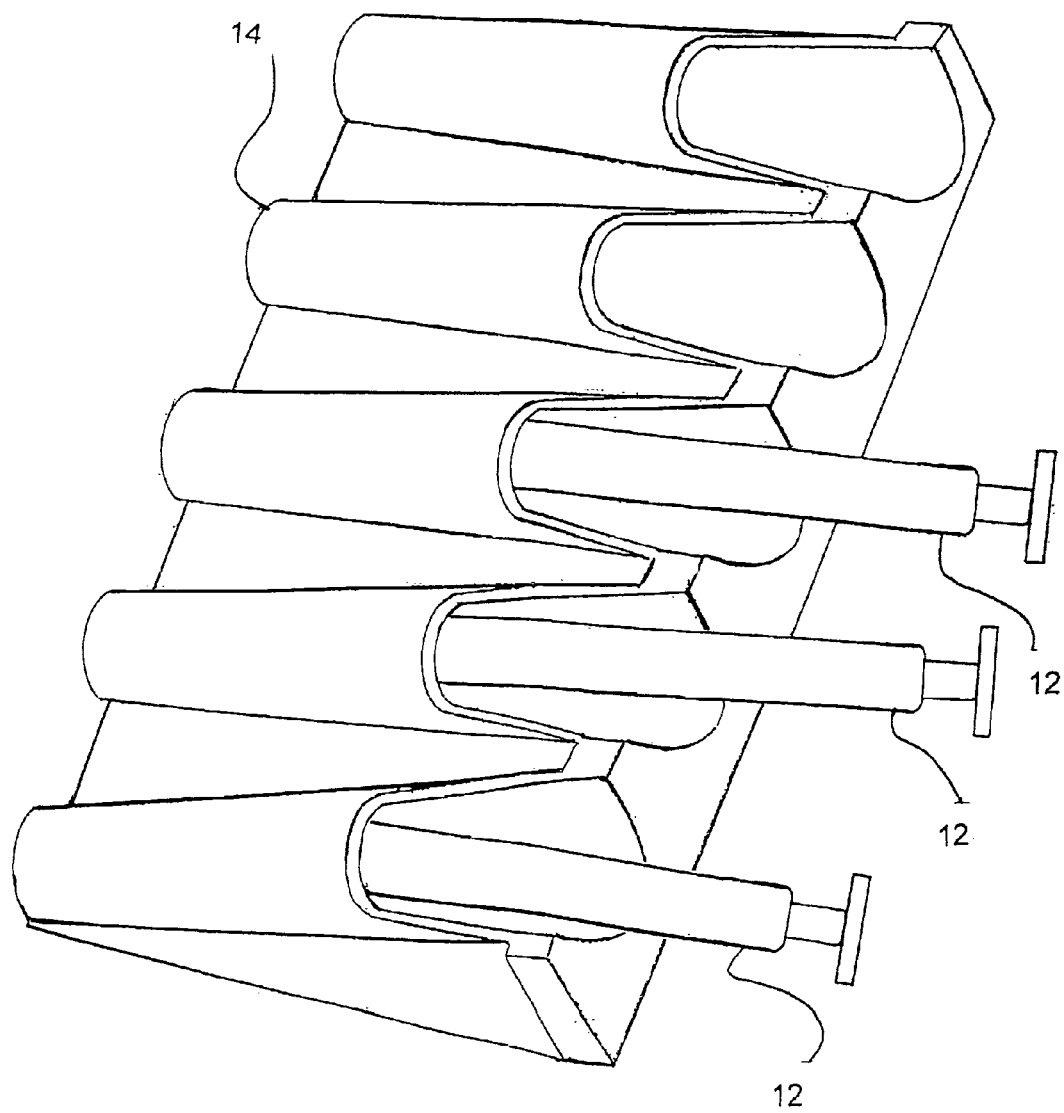
FIG. 11 shows a container for one-handed insertion of used syringe needles wherein they reach a dissolvent gel within for their final disposal.

The FIG. 11 shows a flat holder [14] that has 5 entry point openings for the used syringes [12] to be placed in by a one-handed method, and wherein there would be the disinfectant and dissolvent gel compound that would dissolve each metal needle away forever. This FIG. 11 represents a possible means for a one-handed recapping method that would meet the requirements placed against such activities by a federal mandate.

Figure 12:
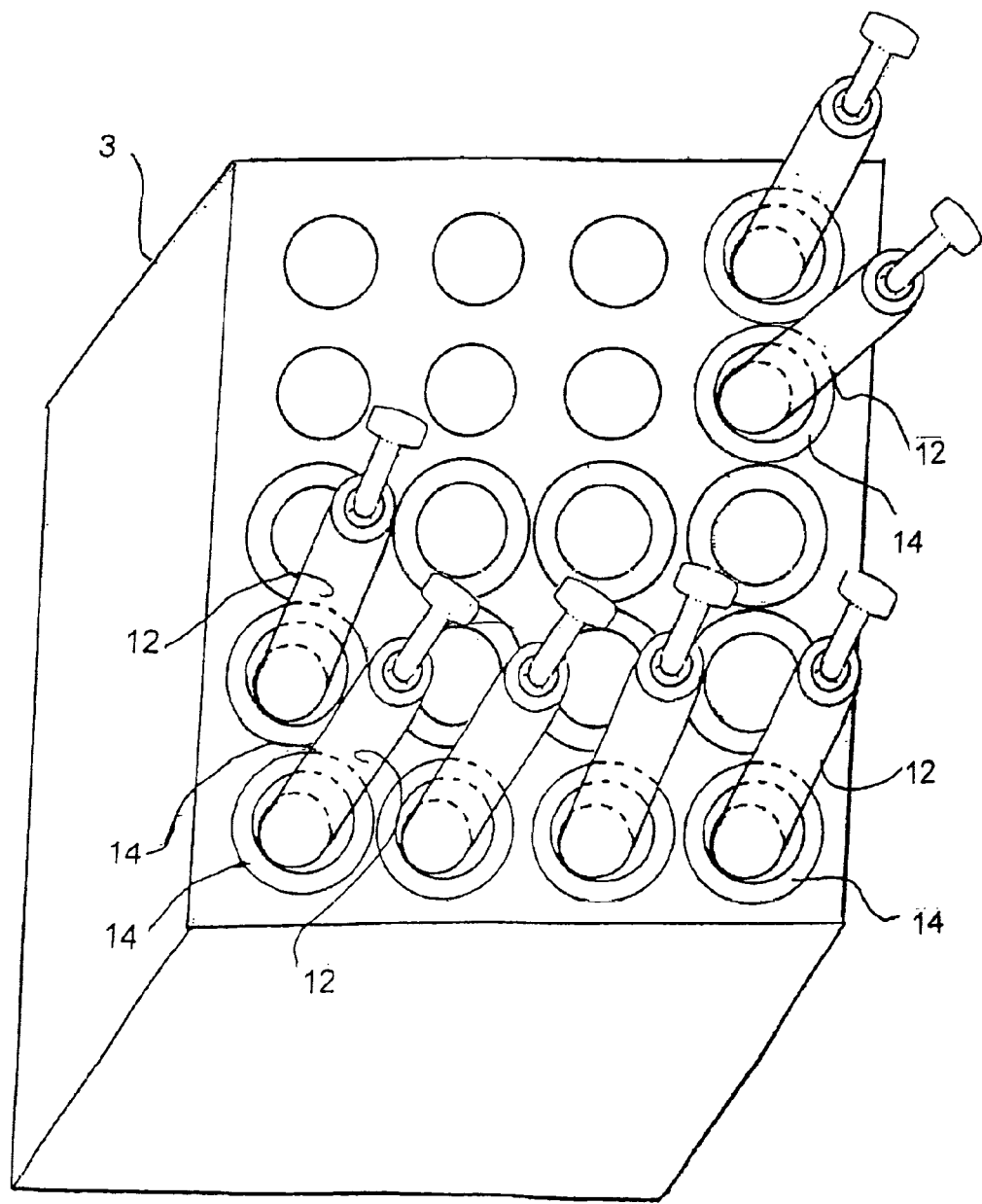
FIG. 12 shows a containment holder for multiple used syringe needles that have been placed in wide-mouth test tube type holders as in FIG. 7 that in turn are put into, or located within, the containment holder herein shown for final disposal.

In the FIG. 12 is shown a container [2] with available multiple holders [14] for possible one-handed containment of used syringes [12] wherein the syringes [12] to be in the holders [14] for disinfecting and dissolving can be stabilized and located while they are to be destroyed by the gel [1].

Figure 13:
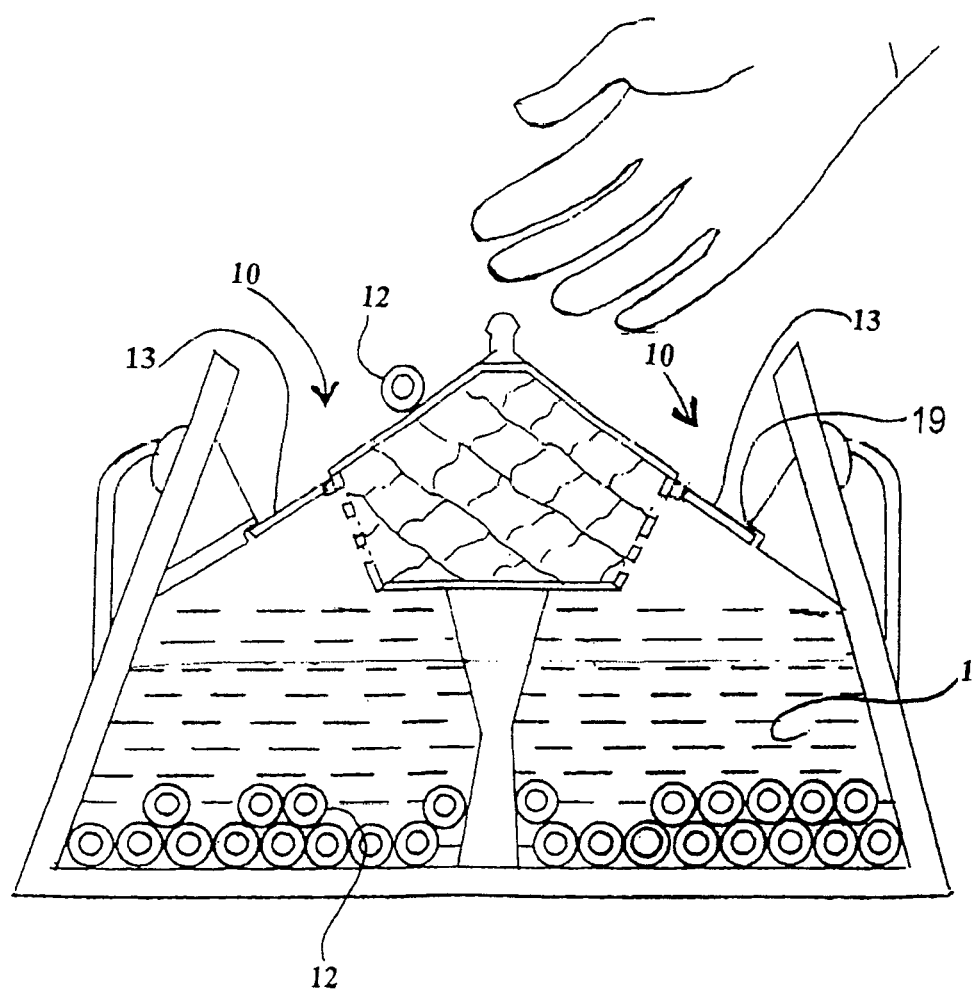
FIG. 13 shows a side view of another type container demonstrating disposal means for multiple used syringe needles

The FIG. 13 shows a more extensive and complex device to contain multiple used syringes [12] in a disinfectant and dissolvent compound [1] to await their final disposal wherein the used syringes [12] are directed into the container through a double entry point [10] and pass into the disinfectant and dissolvent gel [1] by the means of a closing lid [13] that also serves to seal [19] off the container chamber. An additional feature [not numbered] is seen in a filtering section below the entry point that would contain a filtering sponge material to control any odors. Another feature that is shown, but not numbered and may be installed if deemed needed is an opening mechanism to open the selected entry hatch or lid [13] and its seal [19].

Figure 14:
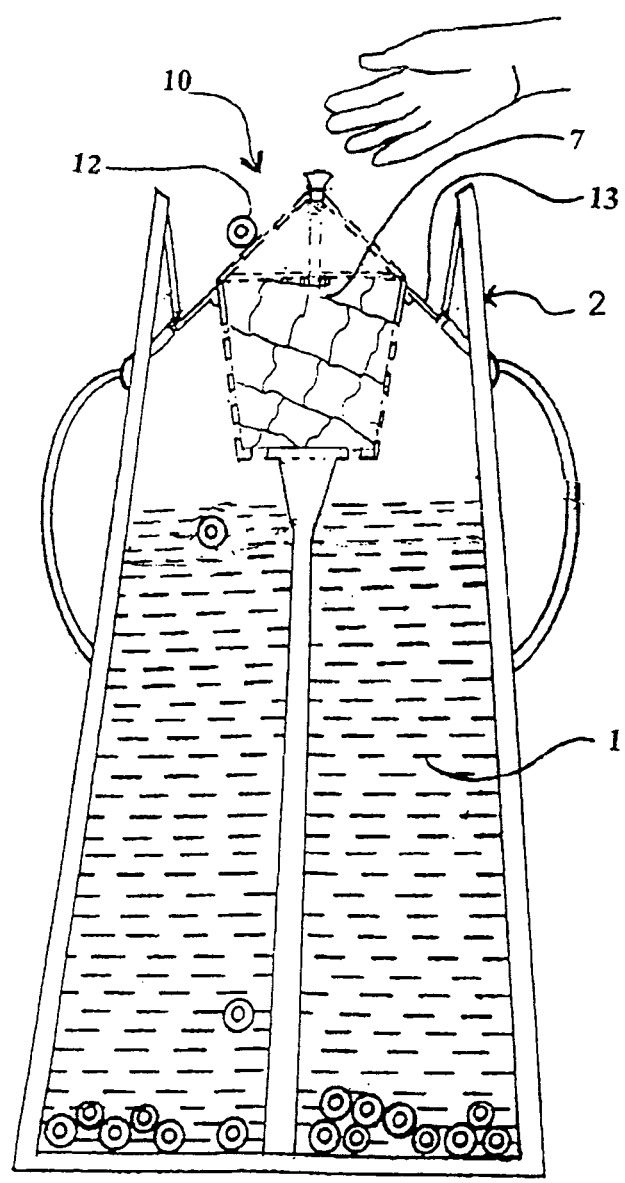
FIG. 14 shows another view of a larger container as in FIG. 13 wherein is shown this dissolvent gel for a safe final disposal of multiple used syringe needles.

This FIG. 14 is a larger model of the prior FIG. 13 with the identical elements the entry point [10] for the used syringes [12] to be placed into the container [2] that holds the disinfectant and dissolvent gel [1]. In this drawing is shown the filter [7] means of sponge intended to gather any odor or smell form the activity of the dissolvent container [2]. The entry point for an individual syringe just as is seen in the FIG. 13, is a closing lid [13] that is located on both sides of the container [2] and herein [not shown numbered] is an elastomeric seal to close off any vapors of the container [2].

Figure 15:
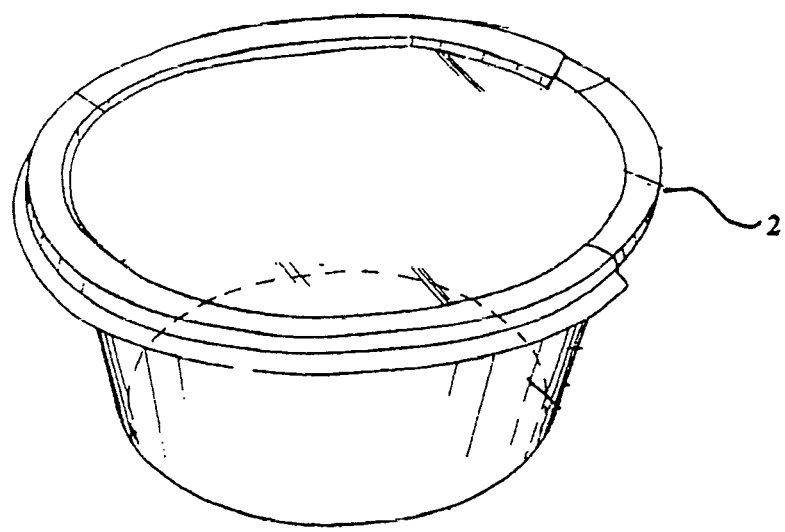
FIG. 15 shows a perspective view of a container being empty to join up with the following FIG. 16 for use containing a dissolvent gel.
Figure 16:
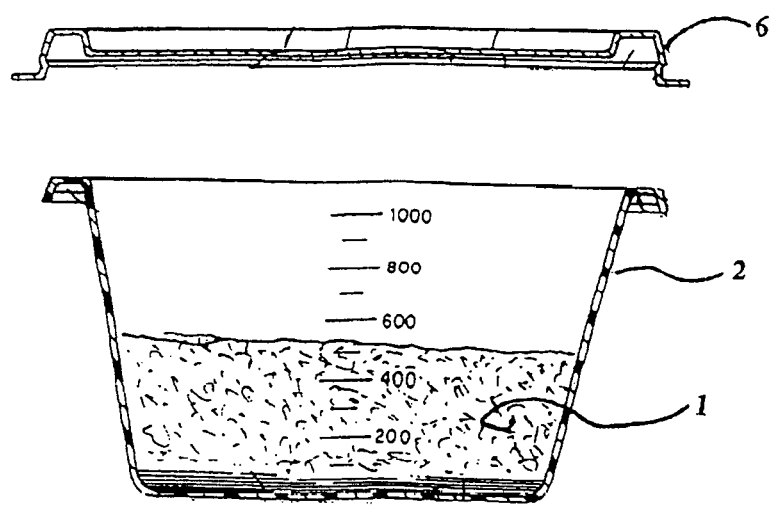
FIG. 16 shows a side view of prior FIG. 15 with its lid and container that can hold a dissolvent gel which can dispose of stainless steel metal hazardous sharps.

In the following FIG. 15 is seen an empty bowl that will be a container [2] for the disinfectant and dissolvent gel compound, and the FIG. 16 to follow is this bowl [2] as the container for the disinfectant and dissolvent gel [1] with its cover being a sealing lid [6].

Figure 17:
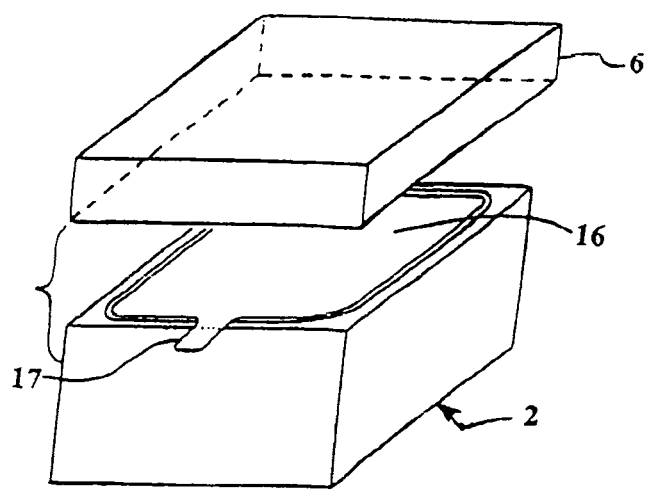
FIG. 17 shows a perspective view of a container and its lid that is seen following in the FIG. 18 that receives the used syringes for disposal.
Figure 18:
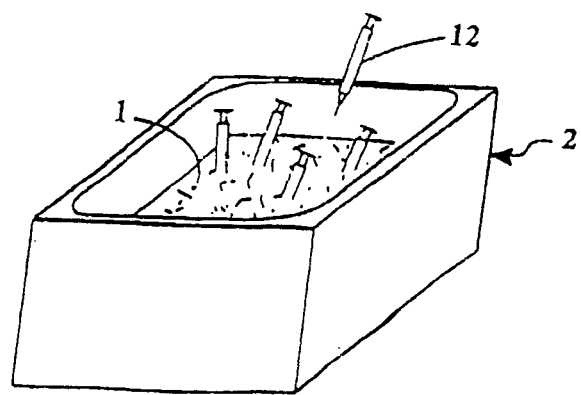
FIG. 18 shows the container of FIG. 17 with the disposal means of a dissolvent gel receiving used syringe needles for final disposal.

In the FIGS. 17 & 18 to follow there is shown a box as a container [2] for the disinfectant and dissolvent gel [1] wherein the used syringes [12] can be placed for disposal. This box container shows a covering lid [6] to place upon the container when all activities are finished and it is ready for disposal. Additionally shown is a tear off sealing cover/lid [17] that is to be removed when first preparing to use the gel to dispose of used sharps and syringes [12].

Figure 19:
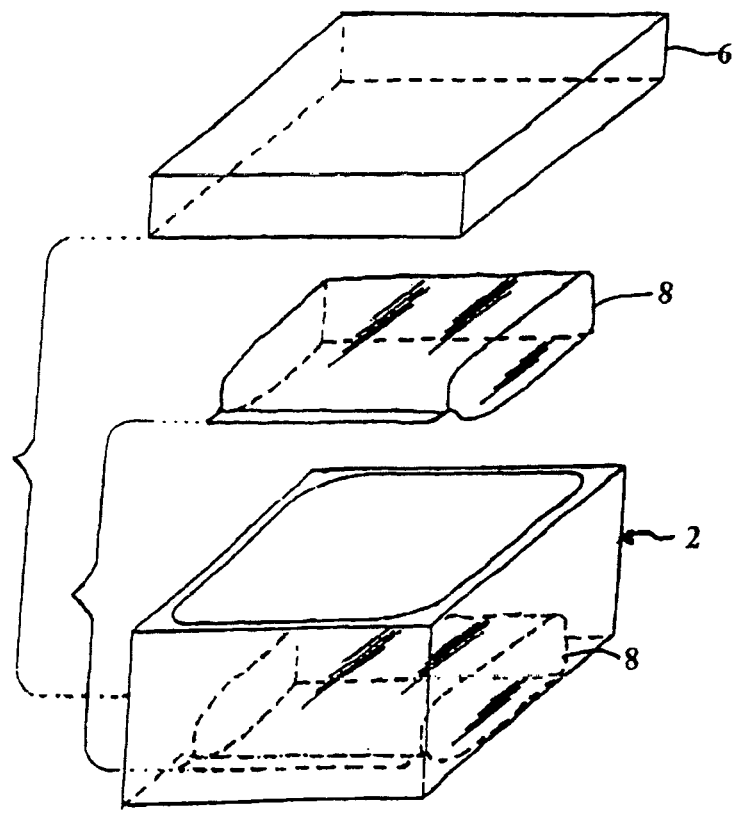
FIG. 19 shows perspective views of a container and its lid with a flexible plastic bag containing a dissolvent gel to be placed inside of the main container to wait for being pierced with used syringe needles as seen in the following FIG. 20.
Figure 20:
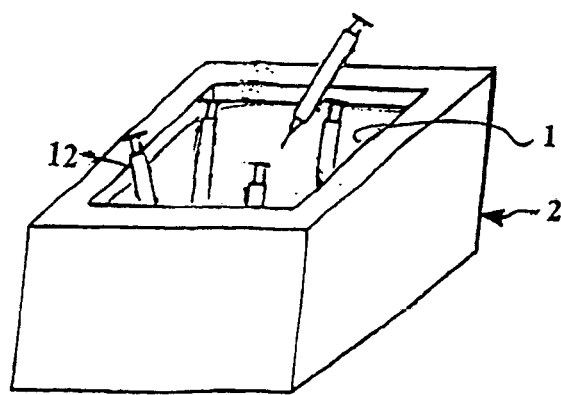
FIG. 20 shows the prior FIG. 19 being used for final disposal of used syringe needles as they are placed inside the container in a dissolvent gel.
Figure 21:
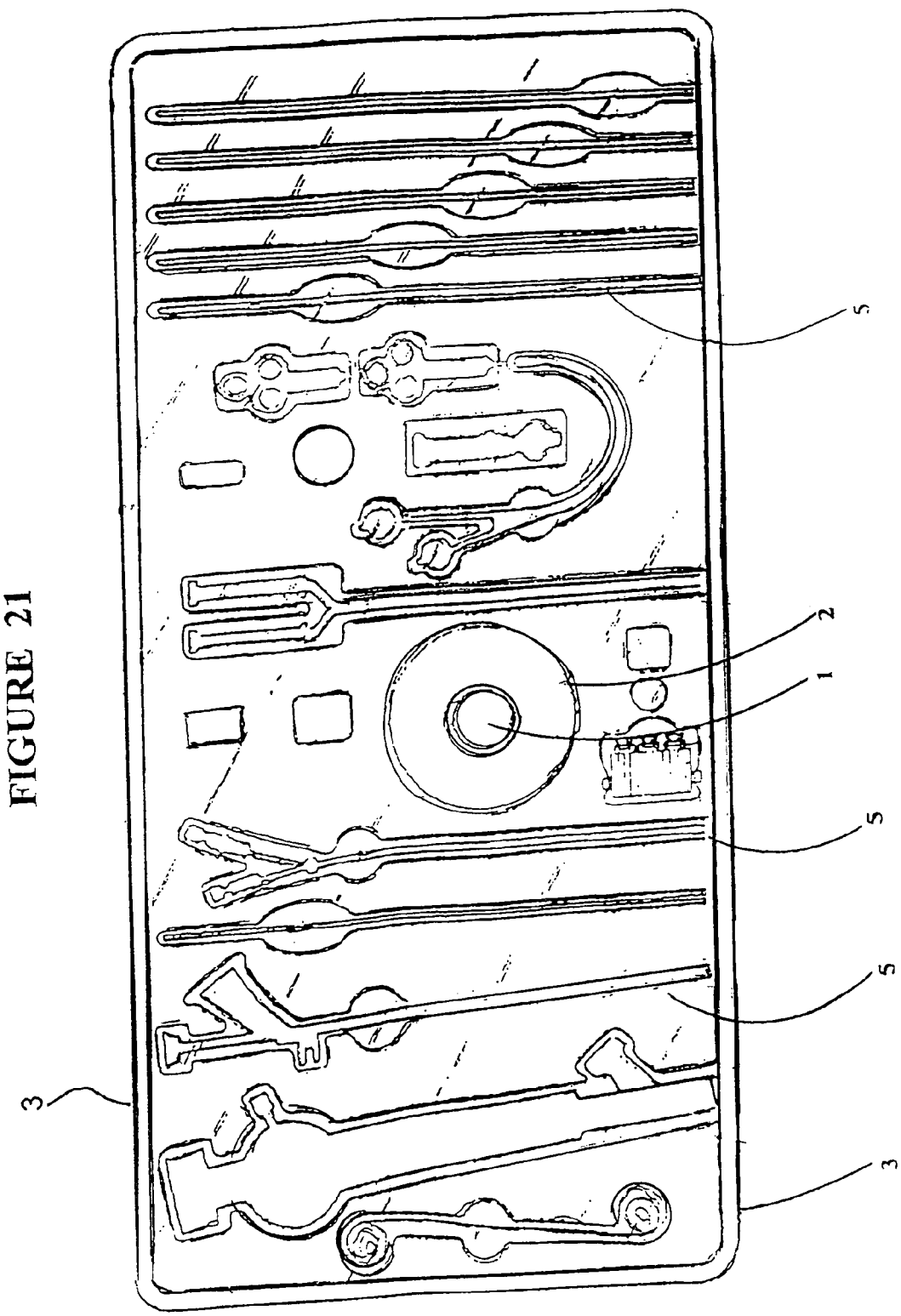
FIG. 21 shows a top view down into a surgical kit that contains disposal means within the kit for final disposal of surgical instrument tips that are demounted and released into the dissolvent gel provided.
Figure 22:
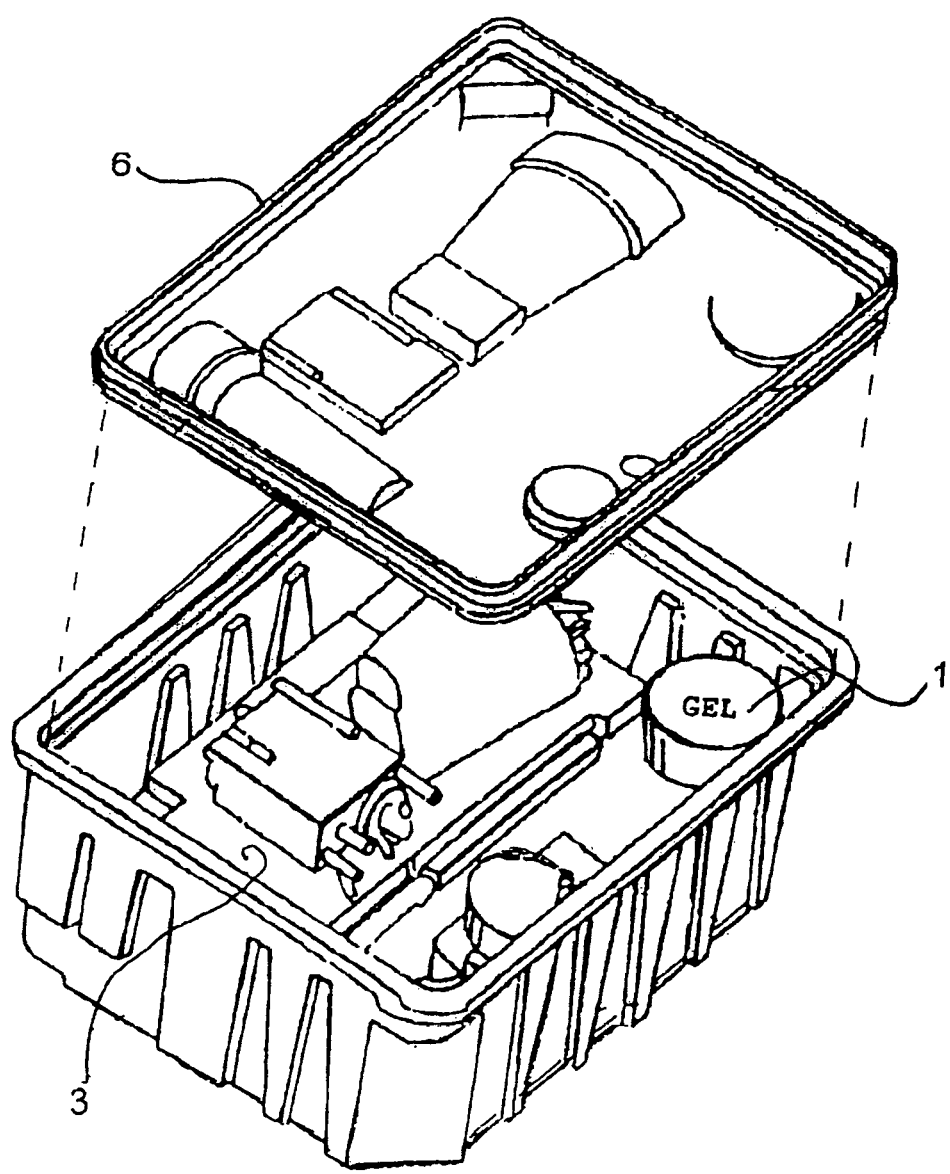
FIG. 22 shows a perspective view of another surgical kit and its lid wherein there is a dissolvent gel provided for convenient final disposal within.
Figure 23:
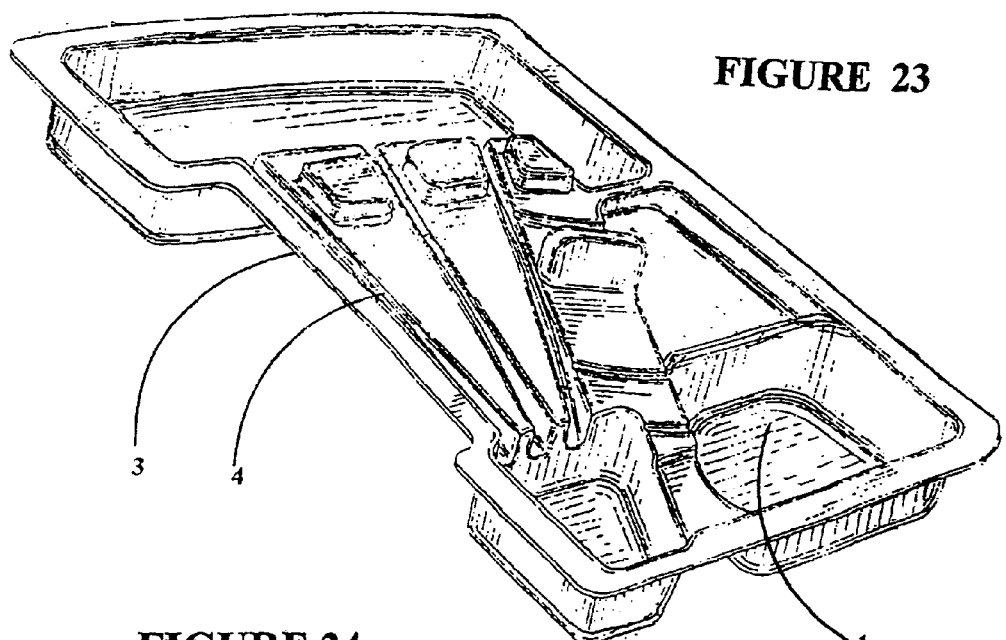
FIG. 23 shows a perspective view of another surgical kit wherein is contained a chamber for the dissolvent gel that will provide a safe and final disposal means for instrument used tips and such.
Figure 24:
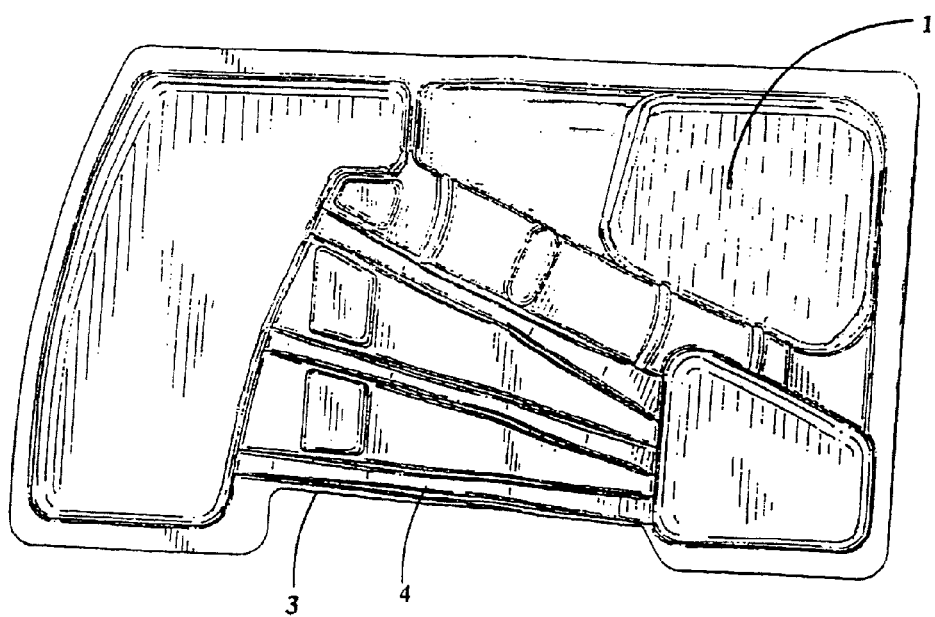
FIG. 24 shows a top view of the surgical kit in FIG. 23 wherein it can be more clearly seen in regard to the chamber that contains the dissolvent gel for used instrument tips.

In the next set of FIGS. 19 & 20 a similar design is shown with a box container [2] and final covering lid [6] to be placed over the box when all used sharps and syringes [12] have been placed inside the disinfectant and dissolvent gel [1] for the final disposal. The one different activity involves a flexible bag or sack [8] that is shown to be placed inside of the box container [2] that contains the disinfectant and dissolvent gel [1] to be used for the dissolving and disposal of the syringes [12].

In the next set of drawings, the FIG. 21 through FIG. 31 there are shown a number of surgical kits [3] as the containers [2] for all surgical tools and instruments [5] possibly needed in a medical operation procedure. These surgical kits have slots or embedded placements [4] wherein the tools or instruments [5] are located at set established positions in every kit [3]. Also, there can be seen placements of the disinfectant and dissolvent means [1] for the final disposal of the items after being used in an operation and oftentimes in a separate container [2] section that is allocated within the kit [3].

Figure 25:
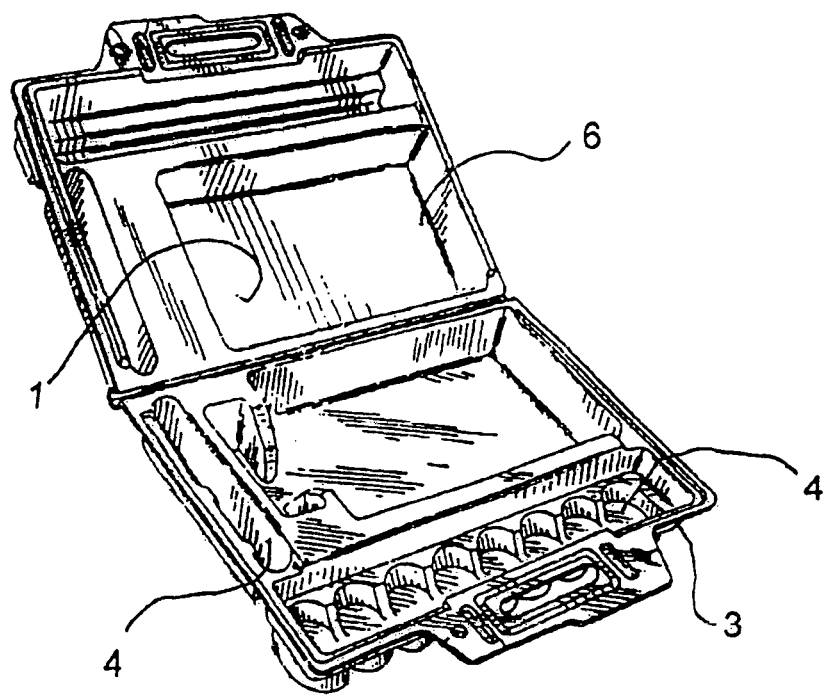
FIG. 25 shows a perspective view of a surgical kit with an attached cover/lid that is open to show the interior that is available for placing the surgical instruments.
Figure 26:
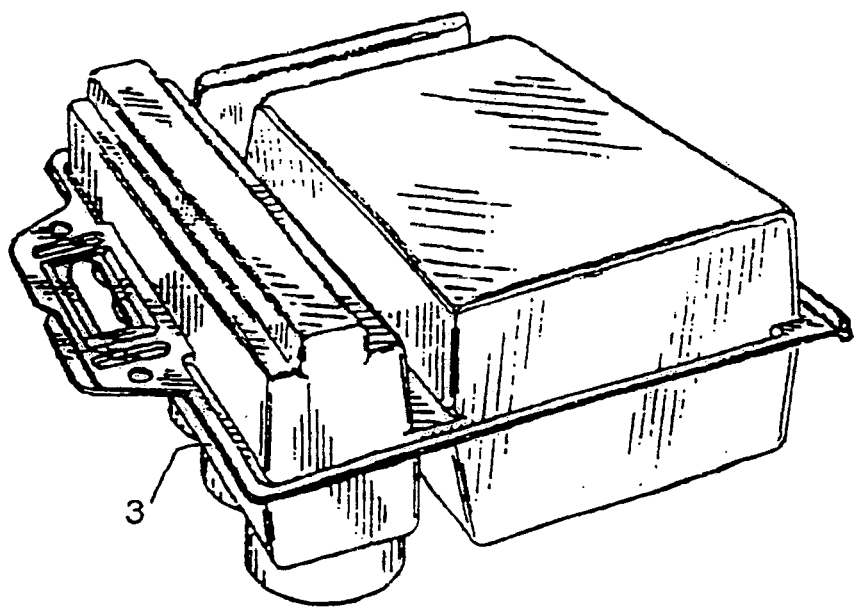
FIG. 26 continues the view of FIG. 25 when closed with its cover in place.
Figure 27:
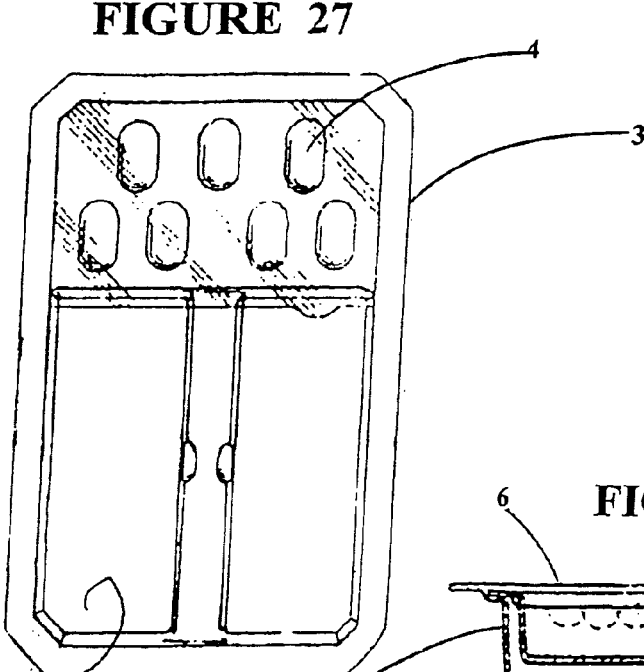
FIG. 27 is a top view looking down into a surgical kit/tray showing the area available for placing the surgical instruments as needed.
Figure 28:
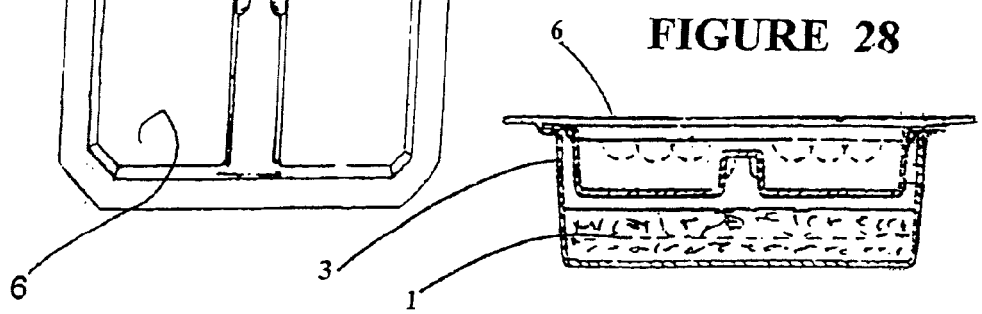
FIG. 28 shows a side end view wherein is outlined the placement of the instruments and the dissolvent gel.
Figure 29:
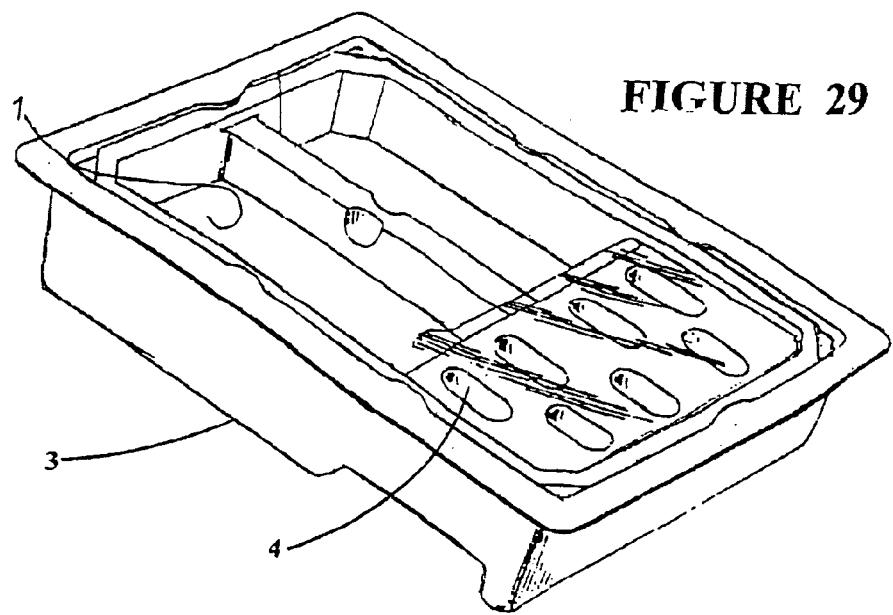
FIG. 29 shows a perspective view from FIG. 27 of the area available for placing the surgical instruments as needed.
Figure 30:
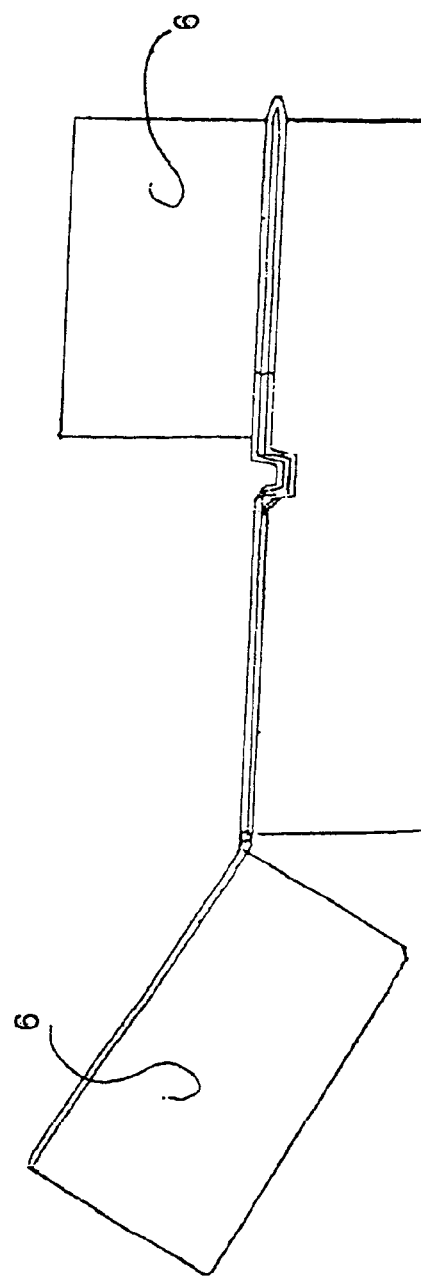
FIG. 30 shows an end view of a surgical kit with one cover opened wherein the dissolvent gel, as a viscous liquid material, would be applied when the cover is tipped over the kit items to be dissolved.
Figure 31:
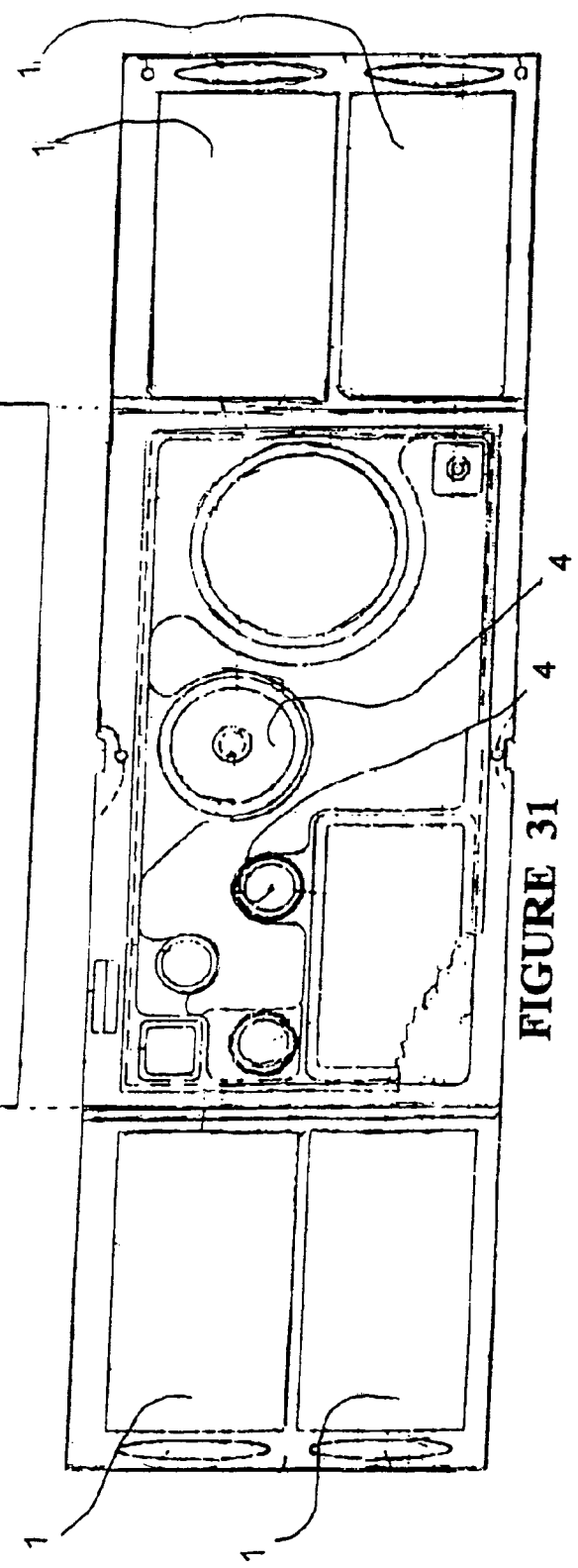
FIG. 31 shows the same surgical kit as in prior FIG. 30 being open to show the placement available for its contents.

In FIG. 25 and FIGS. 30 & 31, the disinfectant and dissolvent gel [1] can be seen in the cover/lid [6] section wherein a sealing cover [not shown] is removed and it is dumped over the kit [3] when the operation is complete. An additional view is seen in the FIGS. 27 & 29 wherein the kit [3] shows a cover/lid [6] that is opened and removed to reveal the gel [1] compound to be accessed for final disposal when the surgery is complete. Thus, in the FIGS. 25, 27, 29, 30, & 31 the final action for disposal is contained within the kit [3], and it is activated once the surgery is completed.

These surgical kits are necessarily complicated and could vary somewhat is final designs, but the main principle in the gel use seems clear to dispose of all tools and instruments deemed to be disposable. In the cases wherein the main function to operate an instrument may be sterilized and reused, then the expendable tip or part is demounted or removed prior to the activity of a final disposal. Each surgical kit [3] can vary as requisite for the occasion at hand, but the action to dispose will remain absolutely final and complete with all infectious material being gone forever.

Figure 32:
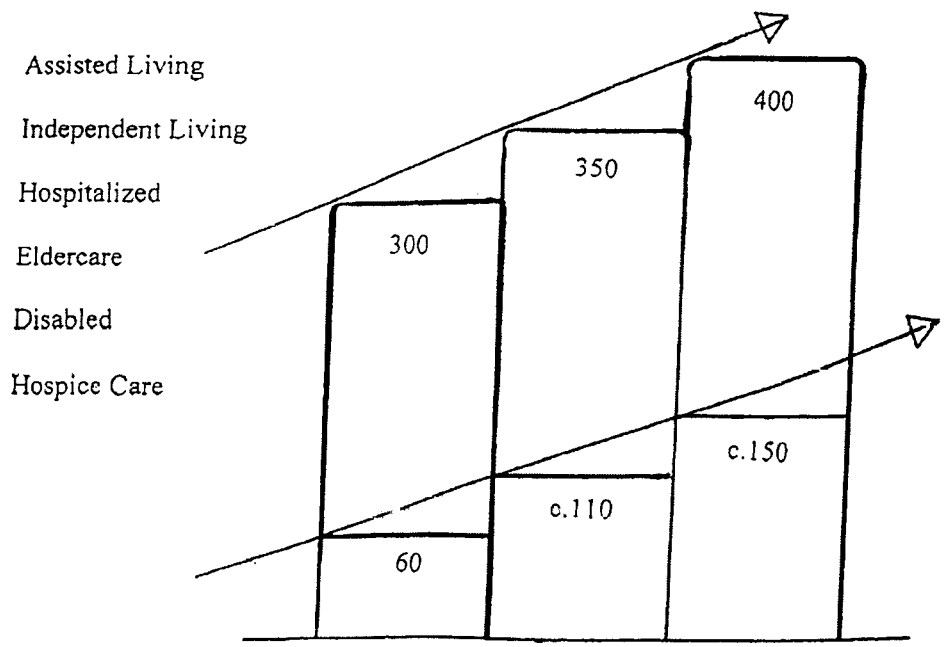
FIG. 32 shows a diagram of 'Medically Assisted Seniors' as they are increasing over the decades ahead indicating an increasing market for the products involving the dissolvent get means.
Figure 33:
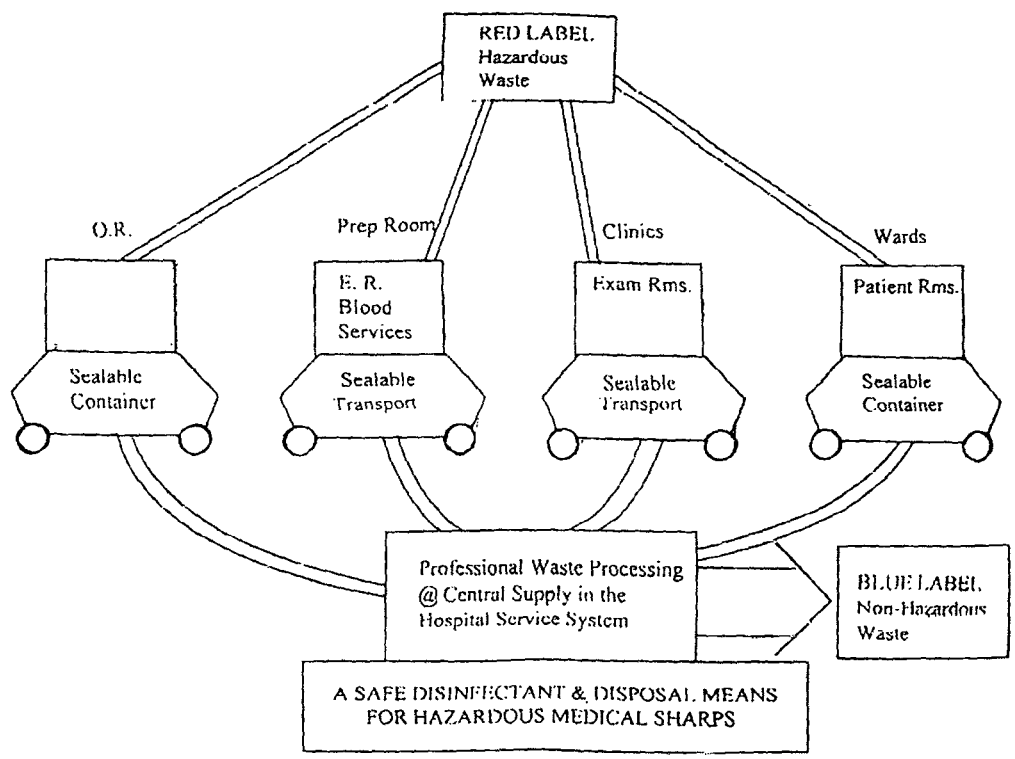
FIG. 33 shows 'Red Label' hazardous waste in a wheel shaped configuration as it proceeds for disposal throughout a hospital environment wherein such hazardous waste can be reduced to 'Blue Label' non-hazardous waste with the appropriate use of the dissolvent gel means.

The final two FIGS. 32 & 33 being shown, present diagrammatic charts that show actions, and emphasize the vastness of the surgical and medical procedures that will continue to increase over the years ahead. In FIG. 32 the continued rise in aging seniors, shows in the chart of 'Medically Assisted Seniors' that can emphasize the increasing need for this invention over the years ahead. In the FIG. 33 is shown the progression from a biologic hazard waste [Red Label] through the various hospital collection stations wherein the medical metal devices are dissolved free of any contaminants and totally disinfected and sterile for final disposal as ordinary waste [Blue Label]. A total risk saving, and cost saving overall, for this safe and final means of disposal is the ultimate gain for this novel and new invention.

EXAMPLE A

Silica Powder Testing Results

Silicone Powder+3 $HCL:3HNO_3$:
1-0.5 g Silicone Powder+4 ml of $3HCL:3HNO_3$
Needle protruded through the gel.
Within seconds turning black along the needle
2 min. forming a thicker darker column
Faint sounding reaction
4½ minutes sludge forming
Needle did not dissolve
2—0.7 g Silicone Powder+6 ml of $3HCL:3HNO_3$
This time the gel covered the whole needle.
Within seconds bubbling and turning black on top
2 min. Black column forming
5½ min. needle broke from plastic hub.
11 min. needle dissolved completely.

EXAMPLE B

Silica Gel Testing Results

Silica Gel Testing
2 g Silica Gel mixed with 2 ml of $3HCL:3HNO_3$
1—Started bubbling immediately
0.5 min. solution started turning from yellow to greenish black
1.35 min. started bubbling furiously
2 min. became VERY HOT
2.30 min needle off plastic hub
2.45 min. needle dissolved completely
2—Added another needle to same solution in the same test-tube
Started bubbling immediately
0.5 min. solution that was still yellow started turning greenish black
3.5 min. needle broke in two
7 min. needle was $\frac{2}{3}^{rds}$ dissolved and reaction diminished
3—Added a third needle to the solution—NOTHING HAPPENED
4 A second tube of silica gel 4 ml of $3HCL:3HNO_3$
This one was very compacted into the test-tube.
Reaction less vigorous and slowed after 2 minutes.
11 min. point off the needle
14 min. ⅓ the needle had dissolved
16 min. stayed the same
Needle did not fully dissolve.
5 A third tube of silica gel+4 ml of $3HCL:3HNO_3$
Bubbling and turning black around the needle w/in seconds
Needle bending at 3 min.
Point gone at 3.4 mm.
Needle off plastic hub at 4.2 mm.
Needle dissolved at 5 min.

Results:

Silica Gel is granular and may be scoring the needle and causing the reaction to initiate and process quicker.

When solution has turned dark green to black the strength of the solution has diminished.

This solution less fumes are emitted than with the liquid acid solutions during the reaction process.

Time for dissolution has been decreased substantially! Best results with liquid acid solutions were 11-16 minutes. With the silica gel+acid solution results are now down to 2½ minutes!!! And 1 and ⅔ needles were dissolved in a combined time of 10 minutes!!!!

EXAMPLE C

Silica Powder & Silica Gel

Testing Results

Silica Gel & Powder Mix Testing—Aug. 3, 2005

1 gram Silica powder:1 gram of Granulated Silica:13 cc on 1HNO3:1HCL mix

Test #1—dissolved in 5 minutes

Test #2—

Reaction darkening w/in seconds

Bendable at 6 minutes

Off plastic hub in 8 minutes

Dissolved in 9 minutes 1 gram Silica powder:0.75 gram of Granulated Silica:13 cc of 1HNO3:1HCL mix Reaction darkening w/in seconds Bendable in 6 minutes Off plastic hub in 8 minutes Dissolved in 9 minutes 1 gram Silica powder:0.50 gram of Granulated Silica:12 cc of 1 HNO3:1 HCL mix Reaction darkening w/in seconds Bendable in 8 minutes Off plastic hub in 9 minutes Dissolved in 10 minutes 1 gram Silica powder:0.25 gram of Granulated Silica:12 cc of 1 HNO3:1 HCL mix Reaction darkening w/in seconds Tip gone in 6 minutes Off plastic hub in 8 minutes Dissolved in 9 minutes

I claim:

1. A medical sharps acidic gel disinfecting and dissolvent composition disposed within a receptacle consisting essentially of inorganic silica, water, acid and a salt.

2. The medical sharps acidic gel disinfectant and dissolvent of claim 1 wherein the said gel disinfecting and dissolving composition renders harmless infectious material or diseases selected from the group consisting of microbes, viruses, pathogens and bacteria.

3. A medical sharps acidic gel disinfecting and dissolvent composition of claim 1 wherein said gel composition dissolves metal medical sharps including syringe needles and cannulas after use.

4. A medical sharps acidic gel disinfecting and dissolvent composition of claim 1, wherein said acidic gel composition dissolves metals of the iron group and steels.

5. A medical sharps acidic gel disinfecting and dissolvent composition of claim 1, wherein said gel dissolvent blunts and corrodes metal medical sharps upon contact with said gel composition.

6. A medical sharps disposal system comprising an acid gel disinfecting and dissolvent composition consisting of inorganic silica, water, acid and a salt and a receptacle for dissolving and sterilizing medical sharps.

7. A medical sharps disposal system of claim 6 wherein the system can be used with surgical kits, at home or in field conditions.

* * * * *